United States Patent
Fu et al.

(10) Patent No.: US 10,301,395 B2
(45) Date of Patent: May 28, 2019

(54) CHEMICALLY-LOCKED BISPECIFIC ANTIBODIES

(71) Applicant: Sorrento Therapeutics, Inc., San Diego, CA (US)

(72) Inventors: Yanwen Fu, San Diego, CA (US); Gunnar F. Kaufmann, San Diego, CA (US); James T. Patterson, San Diego, CA (US)

(73) Assignee: Sorrento Therapeutics, Inc., San Diego, CA (US)

(*) Notice: Subject to any disclaimer, the term of this patent is extended or adjusted under 35 U.S.C. 154(b) by 0 days.

(21) Appl. No.: 15/353,979

(22) Filed: Nov. 17, 2016

(65) Prior Publication Data

US 2017/0137539 A1    May 18, 2017

Related U.S. Application Data

(60) Provisional application No. 62/257,044, filed on Nov. 18, 2015.

(51) Int. Cl.
| | | |
|---|---|---|
| *A61K 39/395* | (2006.01) | |
| *C07K 16/46* | (2006.01) | |
| *C07K 16/28* | (2006.01) | |
| *C07K 16/30* | (2006.01) | |

(52) U.S. Cl.
CPC ........ *C07K 16/468* (2013.01); *C07K 16/2803* (2013.01); *C07K 16/2809* (2013.01); *C07K 16/2827* (2013.01); *C07K 16/2863* (2013.01); *C07K 16/3069* (2013.01); *C07K 2317/31* (2013.01); *C07K 2317/55* (2013.01); *C07K 2317/56* (2013.01); *C07K 2317/73* (2013.01); *C07K 2317/92* (2013.01)

(58) Field of Classification Search
None
See application file for complete search history.

(56) References Cited

U.S. PATENT DOCUMENTS

2015/0165063 A1    6/2015    Flygare et al.
2016/0326266 A1*   11/2016   Fu .................. C07K 16/468

FOREIGN PATENT DOCUMENTS

| WO | 2013/003555 A1 | 1/2013 |
|---|---|---|
| WO | 2014/043403 A1 | 3/2014 |
| WO | 2015/057876 A1 | 4/2015 |
| WO | WO 2015/175357 | * 11/2015 |

OTHER PUBLICATIONS

Ramadoss et al. "An anti-B cell maturation antigen bispecific antibody for multiple myeloma." J Am Chem Soc. 137(16): 5288-91 (2015).
Luo et al. "Noninvasive brain cancer imaging with a bispecific antibody fragment, generated via click chemistry." Proc Natl Acad Sci USA. 112(41):12806-11 (2015).
Kim et al. "Synthesis of bispecific antibodies using genetically encoded unnatural amino acids." J Am Chem Soc. 134(24): 9918-21 (2012).
Hull et al. "Homogeneous bispecifics by disulfide bridging." Bioconjug Chem. 25(8):1395-401 (2014).
Wagner et al. "Bispecific antibody generated with sortase and click chemistry has broad antiinfluenza virus activity," Proc Natl Acad Sci U S A. 111(47): 16820-5 (2014).

* cited by examiner

*Primary Examiner* — Sheela J. Huff
(74) *Attorney, Agent, or Firm* — Womble Bond Dickinson (US) LLP; Danielle L. Herritt; Cristin H. Cowles

(57) ABSTRACT

Provided are bispecific antibody compounds having the Formula I:

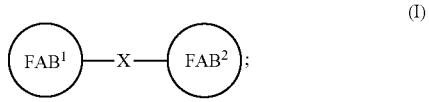

wherein, FAB$^1$, FAB$^2$, and —X— are as defined herein. The provided bispecific antibody compounds can be used a modulators of target molecules, including CD3, PSMA, CD19, CXCR5, CD33, PDL1, VEGFR2, cMet, or Axl, and are useful in the treatment of one or more conditions.

14 Claims, 11 Drawing Sheets
Specification includes a Sequence Listing.

Chemically-Generated Bispecific Fab

CHEMICALLY-LOCKED BISPECIFIC ANTIBODIES

RELATED APPLICATIONS

This application claims the benefit of priority to U.S. Provisional Application No. 62/257,044, filed Nov. 18, 2015.

SEQUENCE LISTING

The instant application contains a Sequence Listing which has been submitted electronically in ASCII format and is hereby incorporated by reference in its entirety. Said ASCII copy, created on Nov. 17, 2016, is named 126036-00402_SL.txt and is 15,301 bytes in size.

BACKGROUND

Bispecific antibodies are antibodies or antibody-like molecules having two different binding specificities. Because of this unique feature, bispecific antibodies not only connect therapeutics (e.g., T cells and drugs) with targets (e.g., tumors), but they can also block separate pathogenic mediators. Clinical successes and impressive treatment profiles against cancer, autoimmune diseases, and inflammatory diseases have been shown. See e.g., MAbs. 2009 November-December; 1(6): 539-547. Given their expanding therapeutic potential, the need for identifying new bispecific antibodies remains.

SUMMARY

It has now been found that bispecific antibody compounds having the general Formula I:

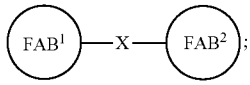

(I)

or a pharmaceutically acceptable salt thereof, and compositions comprising these bispecific antibody compounds, wherein, $FAB^1$, $FAB^2$, and —X— are as defined herein, are effective therapeutics (e.g., in the treatment of cancer. See e.g., FIGS. 9-12.

In addition, the bispecific antibody compounds and compositions described herein can be manufactured in commercially relevant yields and quantities, utilize digestions on off-the-shelf antibodies or cells (e.g., CHO cells), undergo facile conjugation processes, and elicit the exclusive formation of heterodimers (with a high bispecific antibody assembly yield). These processes mitigate conventional requirements for extensive protein engineering of each antibody, complex genetic techniques, and laborious biochemical processing

DETAILED DESCRIPTION

Figure 1:
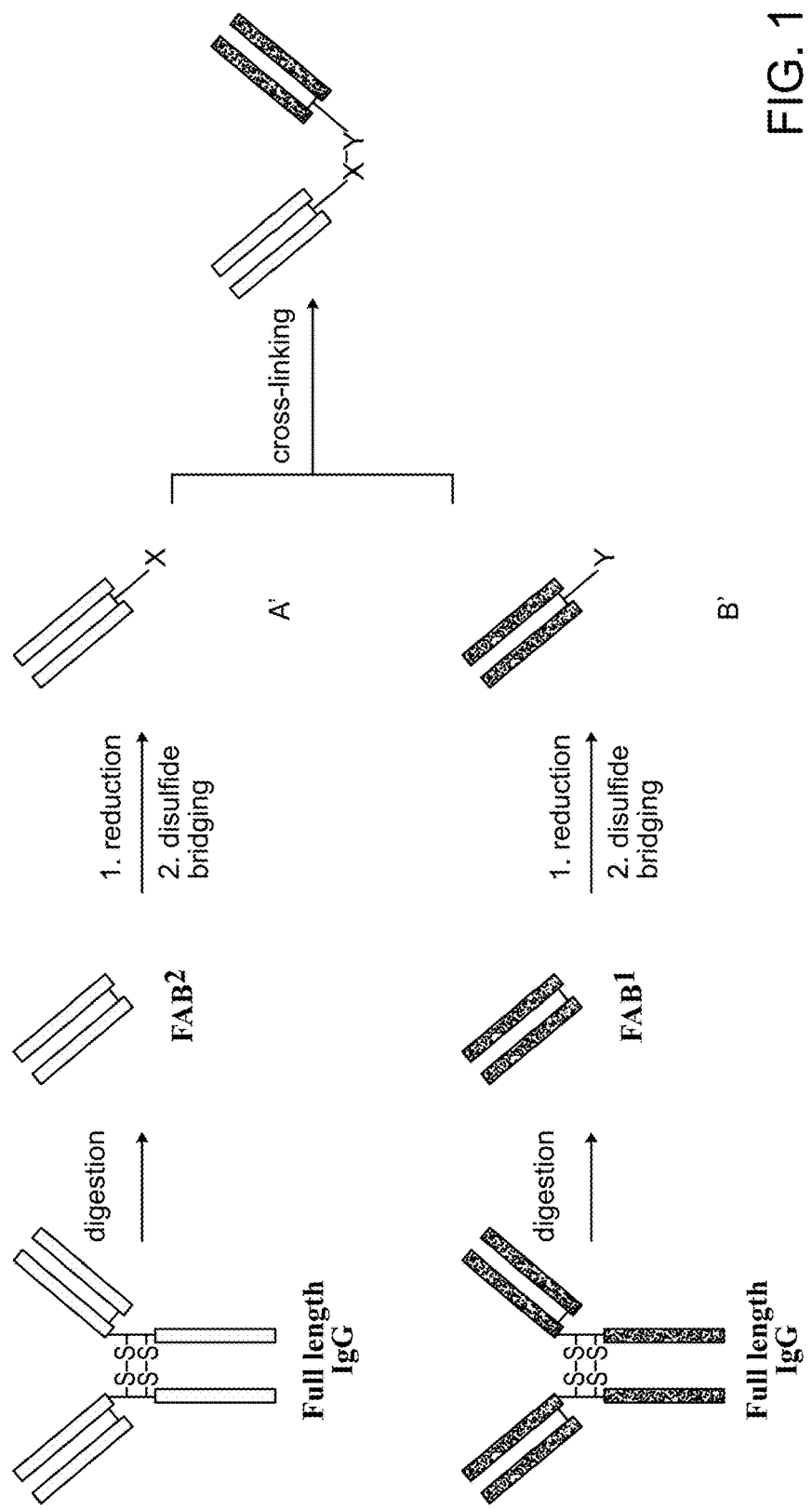
FIG. 1 provides a schematic illustration of the generation of a bispecific antibody compound as described herein.

Provided herein are bispecific antibody compounds having the Formula I:

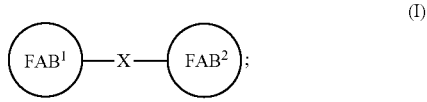

(I)

wherein, $FAB^1$ represents a first Fab fragment; $FAB^2$ represents a second Fab fragment; and —X— represents an optionally substituted triazolyl covalently linking $FAB^1$ and $FAB^2$ together.

Definitions

The term "antibody", as used herein, refers to any immunoglobulin (Ig) molecule comprised of four polypeptide chains, two heavy (H) chains and two light (L) chains, or any functional fragment (e.g., a Fab fragment), mutant, variant, or derivation thereof (e.g., a bispecific antibody compound of Formula I). Such mutant, variant, or derivative antibody formats are known in the art. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG3, IgG4, IgA1 and IgA2) or subclass. In some embodiments, the antibody is a full-length antibody. In some embodiments, the antibody is a murine antibody. In some embodiments, the antibody is a human antibody. In some embodiments, the antibody is a humanized antibody. In other embodiments, the antibody is a chimeric antibody. Chimeric and humanized antibodies may be prepared by methods well known to those of skill in the art including CDR grafting approaches (see, e.g., U.S. Pat. Nos. 5,843,708; 6,180,370; 5,693,762; 5,585,089; and 5,530,101), chain shuffling strategies (see, e.g., U.S. Pat. No. 5,565,332; Rader et al. (1998) PROC. NAT'L. ACAD. SCI. USA 95: 8910-8915), molecular modeling strategies (U.S. Pat. No. 5,639,641)). In one embodiment, the antibodies described herein (e.g., $FAB^1$ and $FAB^2$) do not comprise a hinge region.

The term "bispecific antibody" refers to any immunoglobulin (Ig) molecule comprised of four polypeptide chains, two heavy (H) chains and two light (L) chains, or any functional fragment (e.g., a Fab fragment), mutant, variant, or derivation thereof (e.g., a bispecific antibody compound of Formula I), which can bind to two different epitopes. In one embodiment, the bispecific antibody binds to two different epitopes on the same antigen. In one embodiment, the bispecific antibody binds to epitopes on two different antigens. In one embodiment, the bispecific antibody described herein is of the Formula I, wherein $FAB^1$ and $FAB^2$ do not comprise a hinge region.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) an Fd fragment consisting of the VH and CH1 domains; (iv) a Fv fragment consisting of the VL and VH domains of a single arm of an antibody, (v) and a dAb fragment (Ward et al. (1989) NATURE 341: 544-546; and Winter et al., PCT Publication No. WO 90/05144 A1).

Various techniques are known in the art for the production of antibody fragments. Antibody fragments may be derived via proteolytic digestion of intact antibodies (see, e.g., Morimoto et al., J Biochem Biophys. Method. 24:107-117 (1992); and Brennan et al., Science 229:81 (1985)). Antibody fragments may also be produced directly by recombinant host cells. For example, Fab, Fv and scFv antibody fragments can all be expressed in and secreted from E. coli, thus allowing the facile production of large amounts of these fragments. Antibody fragments can be isolated from the antibody phage libraries discussed below. Such fragments may be conjugated as described herein.

The terms "Fab" or "FAB" or "Fab fragment", as used interchangeably herein, refers to an antibody fragment which is a monovalent fragment having VL, VH, CL and CH1 domains. Unless otherwise specified, a Fab does not contain an Fc region or a hinge region linking the CH1 and CH2 domains of the heavy chain. A F(ab)2 refers to the bispecific antibody compound of Formula I. In one aspect, the terms "$FAB^1$" or "$FAB^2$" refer to a Fab fragment of an antibody. In one aspect, $FAB^1$ and $FAB^2$ do not comprise a hinge region.

The term "human antibody", as used herein, refers to a recombinant antibody having one or more variable and constant regions derived from human immunoglobulin sequences. In one embodiment, all of the variable and constant domains are derived from human immunoglobulin sequences (a fully human antibody). A human antibody may be prepared in a variety of ways, examples of which are described below, including through the immunization with an antigen of interest of a mouse that is genetically modified to express antibodies derived from human heavy and/or light chain-encoding genes.

The term "humanized antibody" refers to an antibody comprising at least one chain comprising variable region framework residues substantially from a human antibody chain (referred to as the acceptor immunoglobulin or antibody) and at least one CDR substantially from a non-human, e.g., a mouse, antibody, (referred to as the donor immunoglobulin or antibody). See, methods of making described in Queen et al., Proc. Natl. Acad. Sci. USA 86:10029 10033 (1989), U.S. Pat. Nos. 5,530,101, 5,585,089, 5,693,761, WO 90/07861, and U.S. Pat. No. 5,225,539, each of which is incorporated by reference herein. The constant region(s), if present, can also be substantially or entirely from a human immunoglobulin. Methods of making humanized antibodies are known in the art. See, e.g., U.S. Pat. No. 7,256,273, incorporated by reference herein. In one embodiment, certain amino acids in the framework and constant domains of the heavy and/or light chains of a non-human species antibody are mutated to produce the humanized antibody. Further examples of how to make humanized antibodies may be found in U.S. Pat. Nos. 6,054,297; 5,886,152; and 5,877,293, each of which is incorporated by reference herein.

An "epitope", as used herein, is the portion of a molecule that is bound by an antibody. In one embodiment, an epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The term "isolated" refers to a molecule that is identified and separated from at least one contaminant molecule with which it is ordinarily associated in the natural source of the molecule. Preferably, the isolated molecule is free of association with all components with which it is naturally associated. In one aspect, the antibodies described are isolated.

As used herein, "substituted triazolyl" refers to a triazoyl group that is substituted with one or more groups that do not substantially alter conditions which allow for the production, detection, and, in certain embodiments, thee recovery, purification, and use for one or more of the bispecific antibody compounds disclosed herein The point of attachment can be on any substitutable position and, include, e.g., 1,2,3-triazolyl (e.g., substituted 1,4; 1,5; 4,5; and 1,4,5) and 1,2,4-triazolyl (e.g., substituted 3,4; 3,5; 4,5; and 3,4,5).

Oxo refers to the functional group "=O" (a substituent oxygen atom connected to another atom by a double bond).

The term "alkyl" means saturated straight-chain or branched monovalent hydrocarbon radical. As used herein a "$(C_2-C_{20})$alkyl" group is means a radical having from 2 to 20 carbon atoms in a linear or branched arrangement. Where defined, alkyl groups may be interrupted by one or more heteroatoms selected from O, N, and S.

The term "alkyne" refers to an an unsaturated hydrocarbon containing at least one carbon—carbon triple bond between two carbon atoms. Terminal alkyne means that the carbon—carbon triple bond between two carbon atoms is at the end of the carbon chain e.g., as in where there is at least one hydrogen atom bonded to a triply bonded carbon atom (e.g., pent-1-yne).

The term "aryl" refers to an aromatic monocyclic or bicyclic carbon ring system having, unless otherwise specified, a total of 6 to 14 ring members. The term "aryl" may be used interchangeably with the term "aryl ring", "aryl group", "aryl moiety," or "aryl radical". Also included within the scope of the term "aryl", as it is used herein, is a group in which an aromatic carbon ring is fused to one or more carbocyclyl rings, e.g., tetrahydronaphthalenyl. In certain embodiments of the present disclosure, "aryl" refers to an aromatic ring system which includes, but is not limited to, phenyl (abbreviated as "Ph"), naphthyl and the like. It will be understood that when specified, optional substituents on an aryl group (e.g., in the case of an optionally substituted aryl or aryl which is optionally substituted) may be present on any substitutable position, i.e., any ring carbon substituted with hydrogen.

The term "heteroaryl" used alone or as part of a larger moiety as in "heteroarylalkyl", "heteroarylalkoxy", or "heteroarylaminoalkyl", refers to a 5-10 -membered aromatic radical containing 1-4 heteroatoms selected from N, quaternary ammonium cation, O, and S, and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". Nonlimiting examples include indolyl, indazolyl, benzimidazolyl, benzthiazolyl, pyrrolopyridinyl, quinolyl, quinazolinyl, and quinoxalinyl. It will be understood that when specified, optional substituents on a heteroaryl group may be present on any substitutable position (carbon and nitrogen).

The term "carbocyclyl" as used herein, means a monocyclic, bicyclic (e.g., a bridged or spiro bicyclic ring), polycyclic (e.g., tricyclic or more), or fused hydrocarbon ring system that is completely saturated or that contains one or more units of partial unsaturation, but where there is no aromatic ring. Cycloalkyl is a completely saturated carbocycle. Monocyclic carbocyclyl groups include, without limitation, cyclopropyl, cyclobutyl, cyclopentyl, cyclopentenyl, cyclohexyl, cyclohexenyl, cycloheptyl, cycloheptenyl, and cyclooctyl. Bridged bicyclic carbocyclyl groups include, without limitation, bicyclo[3.2.1]octane, bicyclo[2.2.1]heptane, bicyclo[3.1.0]hexane, and the like. Spiro bicyclic carbocyclyl groups include, e.g., spiro[3.6]decane, spiro[4.5]decane, and the like. Fused carbocyclyl rings include, e.g., decahydronaphthalene, octahydropentalene, and the like. Polycyclic carbocyclyl rings include e.g., bicyclo[6.1.0]nonane and 1,4,5,5a,6,6a,7,8-octahydrocyclopropa[5,6]cycloocta[1,2-d][1,2,3]triazole. It will be understood that when specified, optional substituents on a carbocyclyl (e.g., in the case of an optionally substituted carbocyclyl or carbocyclyl which is substituted) may be present on any substitutable position and, include, e.g., the position at which the carbocyclyl group is attached.

The term "heterocyclyl" means a 3-12 membered (e.g., a 4-, 5-, 6-7-and 8-membered) saturated or partially unsaturated heterocyclic ring containing 1 to 4 heteroatoms independently selected from N, O, and S. It can be monocyclic, bicyclic (e.g., a bridged, fused, or Spiro bicyclic ring), or polycyclic (e.g., tricyclic or more). The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, 3-azabicyclo[3.1.0] hexanyl, 2-oxa-6-azaspiro[3.3]heptanyl, 1-azaspiro[4.5] decane, and tetrahydropyrimidinyl. The term "heterocyclyl" also includes, e.g., unsaturated heterocyclic radicals fused to another unsaturated heterocyclic radical or aryl or heteroaryl ring, such as for example, tetrahydronaphthyridine, indolinone, dihydropyrrolotriazole, imidazopyrimidine, quinolinone, and dioxaspirodecane. Examples of polycyclic (e.g., tricyclic or more) heterocyclyl include, without limitation, 5,6,11,12-tetrahydrodibenzo[b,f]azocine and 8,9-dihydro-1H-dibenzo[b,f][1,2,3]triazolo[4,5-d]azocine. It will also be understood that when specified, optional substituents on a heterocyclyl group may be present on any substitutable position and, include, e.g., the position at which the heterocyclyl is attached (e.g., in the case of an optionally substituted heterocyclyl or heterocyclyl which is optionally substituted).

The term "spiro" refers to two rings that share one ring atom (e.g., carbon).

The term "fused" refers to two rings that share two adjacent ring ring atoms.

The term "bridged" refers to two rings that share at least three ring atoms.

As described herein, the moieties present on the substituted triazolyl may be further substituted or contain "optionally substituted" moieties. For example, optionally substituted alkyl, optionally substituted pyrazolyl, an optionally substituted carbocyclic, an optionally substituted substituted multi-cyclic heterocyclic ring system, etc. Unless otherwise indicated, an "optionally substituted" group may have a suitable substituent that results in the formation of stable or chemically feasible compounds. The term "stable", as used herein, refers to groups that are not substantially altered when subjected to conditions to allow for their production, detection, and, in certain embodiments, their recovery, purification, and use for one or more of the purposes disclosed herein.

In one aspect, suitable substituents for an optionally substituted or substituted alkyl, carbocyclyl, or heterocyclyl group are those which do not substantially diminish the yield of the bispecific antibody comopund. Examples include halogen, CN, —$OR^c$, —$NR^dR^e$, —$S((O)_iR^c$, —$NR^cS(O)_2$ $R^c$, —$S(O)_2NR^dR^e$, —$C(=O)OR^c$, —$OC(=O)OR^c$, —$OC(=O)R^c$, —$OC(=S)OR^c$, —$C(=S)OR^c$, —$O(C=S)R^c$, —$C(=O)NR^dR^e$, —$NR^cC(=O)R^c$, —$C(=S)NR^dR^e$, —$NR^cC(=S)R^c$, —$NR^c(C=O)OR^c$, —$O(C=O)NR^dR^e$, —$NR^c(C=S)OR^c$, —$O(C=S)NR^dR^e$, —$NR^c(C=O)$ $NR^dR^e$, —$NR^c(C=S)NR^dR^e$, —$C(=S)R^c$, —$C(=O)R^c$, $(C_1-C_6)$alkyl, cycloalkyl, —$(CH_2)_{1-4}$-cycloalkyl, heterocyclyl, —$(CH_2)_{1-4}$-heterocyclyl, aryl, —NHC(=O)-heterocyclyl, —NHC(=O)-cycloalkyl, —$(CH_2)_{1-4}$-aryl, heteroaryl or —$(CH_2)_{1-4}$-heteroaryl, wherein each of said $(C_1-C_6)$alkyl, cycloalkyl, —$(CH_2)_{1-4}$-cycloalkyl, heterocyclyl, —$(CH_2)_{1-4}$- heterocyclyl, aryl, —$(CH_2)_{1-4}$-aryl, heteroaryl and —$(CH_2)_{1-4}$-heteroaryl are optionally substituted with halogen, $OR^c$, —$NO_2$, —CN, —$NR^cC(=O)R^c$, —$NR^dR^e$, —$S(O)_kR^c$, —$C(=O)OR^c$, —$C(=O)NR^dR^e$, —$C(=O)R^c$, $(C_1-C_3)$alkyl, halo$(C_1-C_3)$alkyl, $(C_1-C_3)$alkoxy$(C_1-C_3)$ alkyl, $(C_1-C_3)$alkoxy, and halo$(C_1-C_3)$alkoxy, wherein $R^c$ is hydrogen or $(C_1-C_6)$alkyl optionally substituted with 1 to 3 halogen; $R^d$ and $R^e$ are each independently selected from hydrogen and $(C_1-C_6)$alkyl; and k is 0, 1 or 2. Suitable substituents for optionally substituted alkyl, carbocyclyl, and heterocyclyl also include oxo (=O).

The bispecific antibody compounds described herein may be present in the form of pharmaceutically acceptable salts. For use in medicines, pharmaceutically acceptable salts refer to non-toxic pharmaceutically acceptable salts. Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Suitable pharmaceutically acceptable basic salts include e.g., ammonium salts, alkali metal salts (such as sodium and potassium salts) and alkaline earth metal salts (such as magnesium and calcium salts).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Bispecific Antibody Compounds and Methods of Making Same

In a first exemplary embodiment, the bispecific antibody compounds of Formula I are of the Formula II, IIa, III, or IIIa:

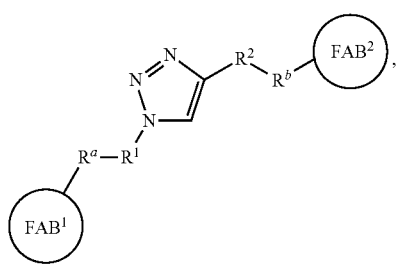

(II)

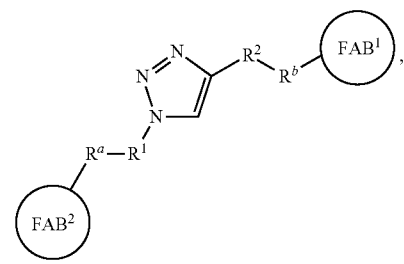

(IIa)

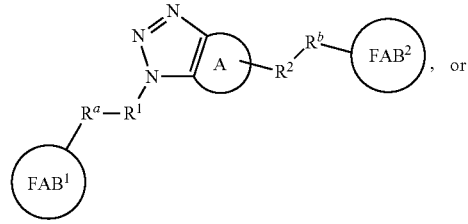

(III)

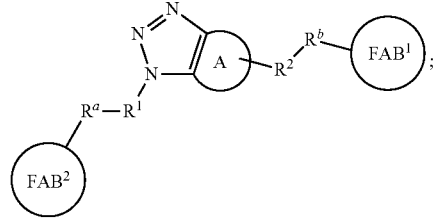

(IIIa)

wherein $R^1$ and $R^2$ are each independently a substituted alkyl; ring A is a substituted carbocyclyl or substituted heterocyclyl; and $R^a$ and $R^b$ are each independently selected from

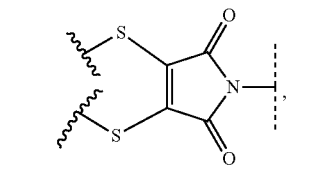

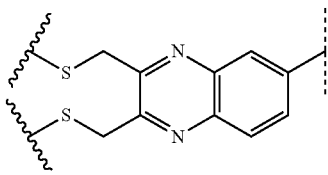

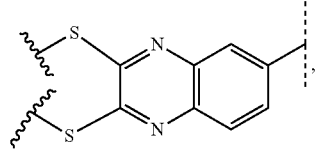

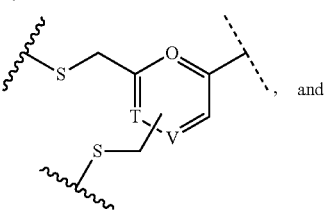

, and

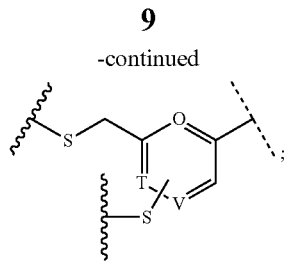

wherein Q, T, and V are each independently N or CH; "∿∿" indicates the points of attachment to FAB[1] or FAB[2] and "-----" indicates the point of attachment to $R^1$ or $R^2$, and wherein the remaining variables and values are as described for Formula I.

In a second exemplary embodiment, Ring A in Formula I, III, or IIIa is a substituted bicyclic or polycyclic carbocyclyl or a substituted polycyclic heterocyclyl, wherein the remaining variables and values are as described for Formula I or the first exemplary embodiment.

In a third exemplary embodiment, Ring A is

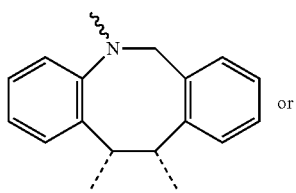

or wherein the dashed bonds indicate the points of attachment to the triazolyl and the wavy bond indicates the attachment to $R^2$, and wherein the remaining variables and values are as described for Formula I or the first or second exemplary embodiment.

In a fourth exemplary embodiment, $R^1$ and $R^2$ in Formula I, II, IIa, III, or IIIa are each independently an optionally substituted $(C_2$-$C_{30})$alkyl optionally interrupted with one or more heteroatoms selected from N, O, and S, wherein the remaining variables and values are as described for Formula I or the first, second, or third exemplary embodiment.

In a fifth exemplary embodiment, $R^1$ and $R^2$ in Formula I, II, IIa, III, or IIIa are each independently a substituted $(C_2$-$C_{30})$alkyl optionally interrupted with one or more heteroatoms selected from N and O, wherein the remaining variables and values are as described for Formula I or the first, second, third, or fourth exemplary embodiment.

In a sixth exemplary embodiment, $R^1$ and $R^2$ in Formula I, II, IIa, , III, or IIIa are each independently a $(C_2$-$C_{30})$alkyl interrupted with at least one O and at least one N, and substituted with at least one oxo, wherein the remaining variables and values are as described for Formula I or the first, second, third, fourth, or fifth exemplary embodiment.

In a seventh exemplary embodiment, $R^1$ and $R^2$ in Formula I, II, IIa, , III, or IIIa are each independently selected from

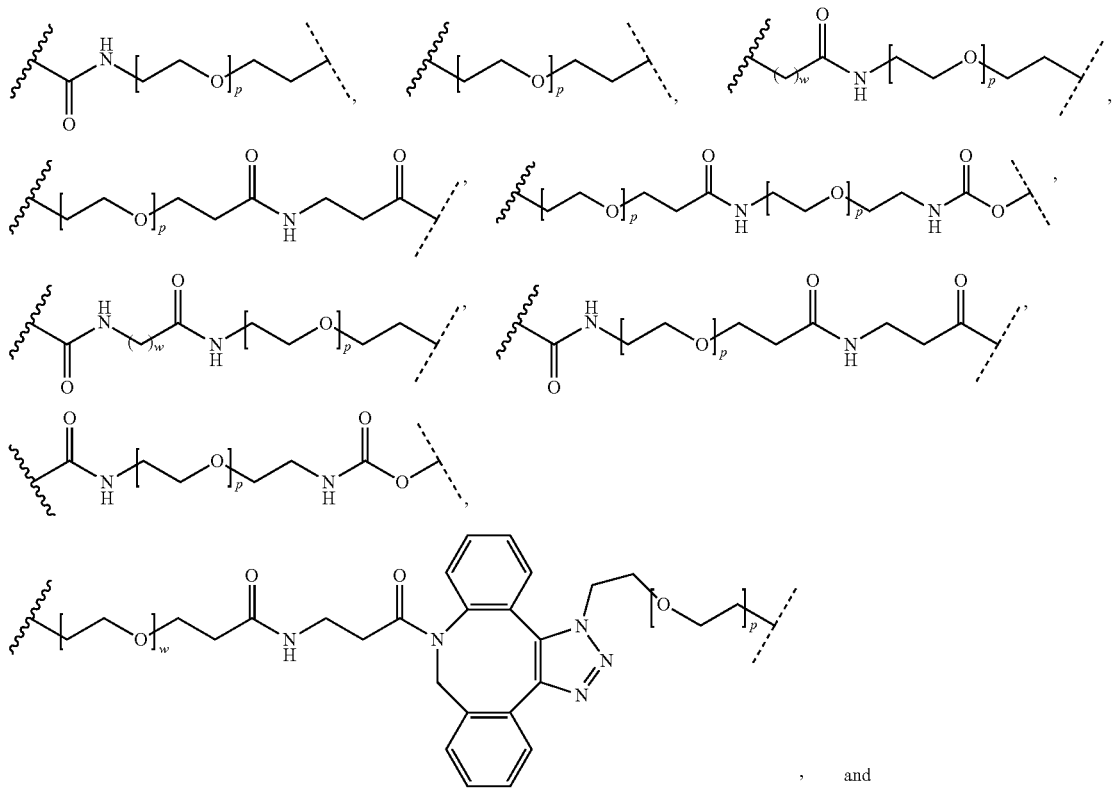

, and

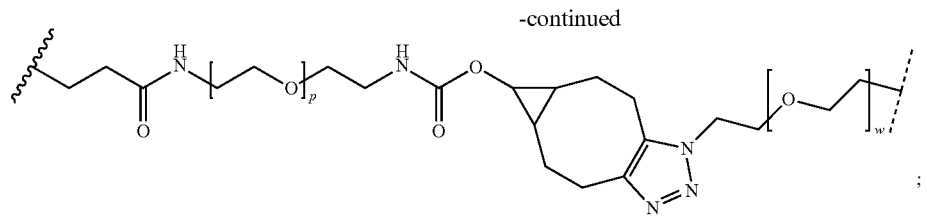

the wavy lines indicate the points of attachment to $R^a$ or $R^b$; the dashed lines indicated the points of attachment to the triazolyl or ring A; and p and w independently are integers from 1 to 8, wherein the remaining variables and values are as described for Formula I or the first, second, third, fourth, fifth, or sixth exemplary embodiment.

In an eighth exemplary embodiment, $R^1$ in Formula I, II, IIa, III, or IIIa is selected from

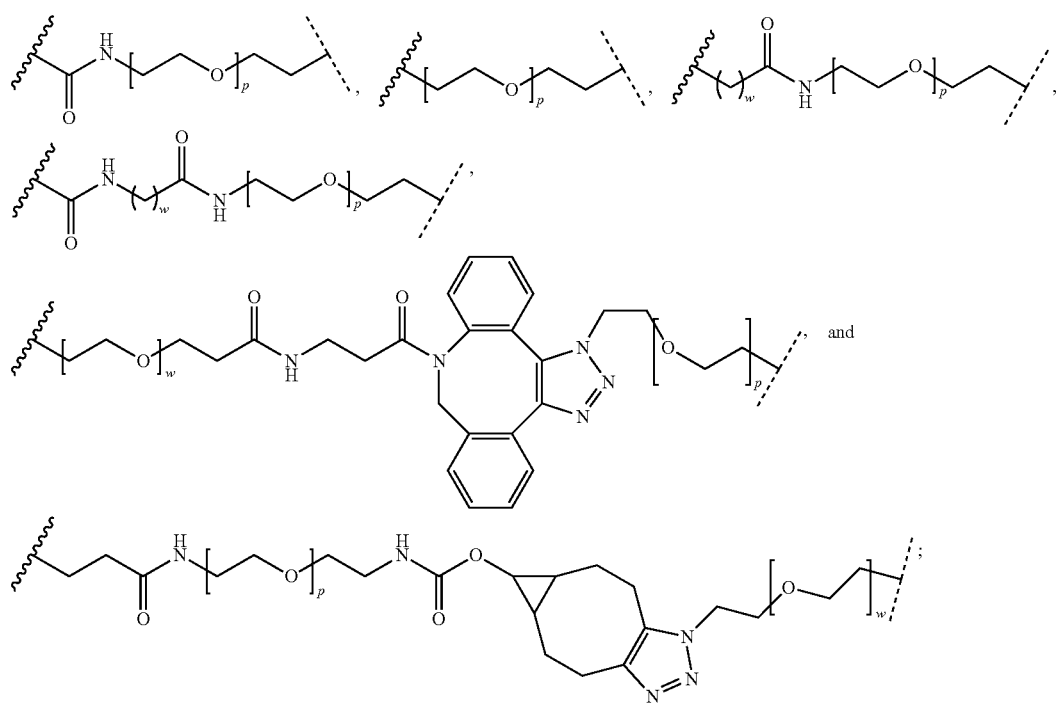

wherein the wavy lines indicate the points of attachment to $R^a$; and the dashed lines indicated the points of attachment to the triazolyl, and wherein the remaining variables and values are as described for Formula I or the first, second, third, fourth, fifth, sixth, or seventh exemplary embodiment.

In a ninth exemplary embodiment, $R^2$ in Formula I, II, IIa, III, or IIIa is selected from

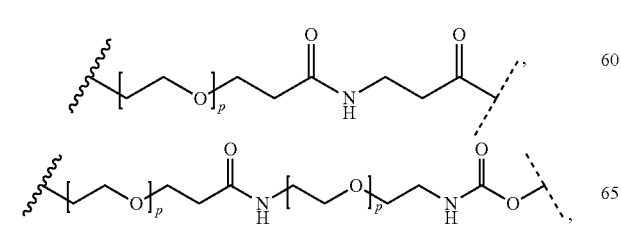

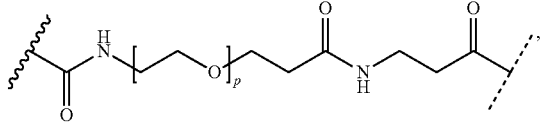

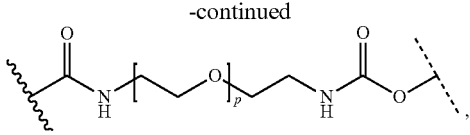

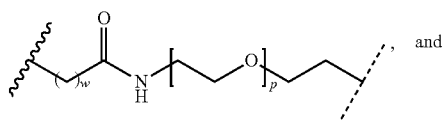, and

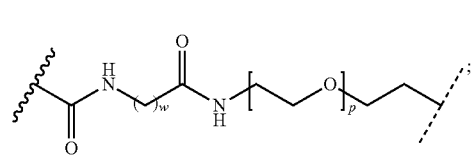;

the wavy lines indicate the points of attachment to $R^a$; and the dashed lines indicated the points of attachment to the triazolyl or ring A, wherein the remaining variables and values are as described for Formula I or the first, second, third, fourth, fifth, sixth, seventh, or eighth exemplary embodiment.

In a tenth exemplary embodiment, $R^a$ and $R^b$ in Formula I, II, IIa, , III, or IIIa are bound to $FAB^1$ and $FAB^2$ through native cysteines of $FAB^1$ and $FAB^2$, wherein the remaining variables and values are as described for Formula I or the first, second, third, fourth, fifth, sixth, seventh, eighth, or ninth exemplary embodiment. Alternatively, $R^a$ and $R^b$ in Formula I, II, IIa, , III, or IIIa are bound to $FAB^1$ and $FAB^2$ through native cysteines that are responsible for forming interchain disulfide bonds of $FAB^1$ and $FAB^2$, wherein the remaining variables and values are as described for Formula I or the first, second, third, fourth, fifth, sixth, seventh, eighth, or ninth exemplary embodiment.

In an eleventh exemplary embodiment, the bispecific antibody compound of Formula I is of the formula:

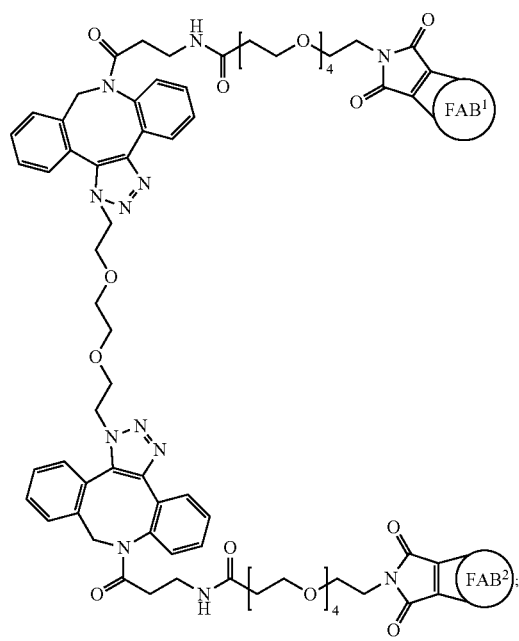

or a pharmaceutically acceptable salt thereof, wherein $FAB^1$ and $FAB^2$ are connected to the pyrrolidine-dione through native cysteine residues.

In a thirteenth embodiment, the bispecific antibody compound of Formula I is of the formula:

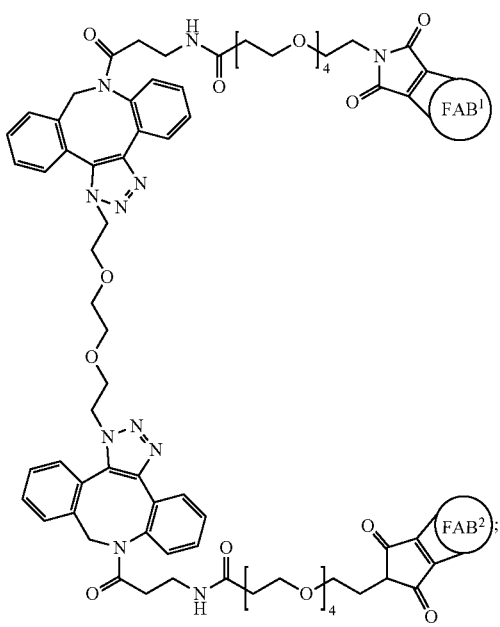

-continued

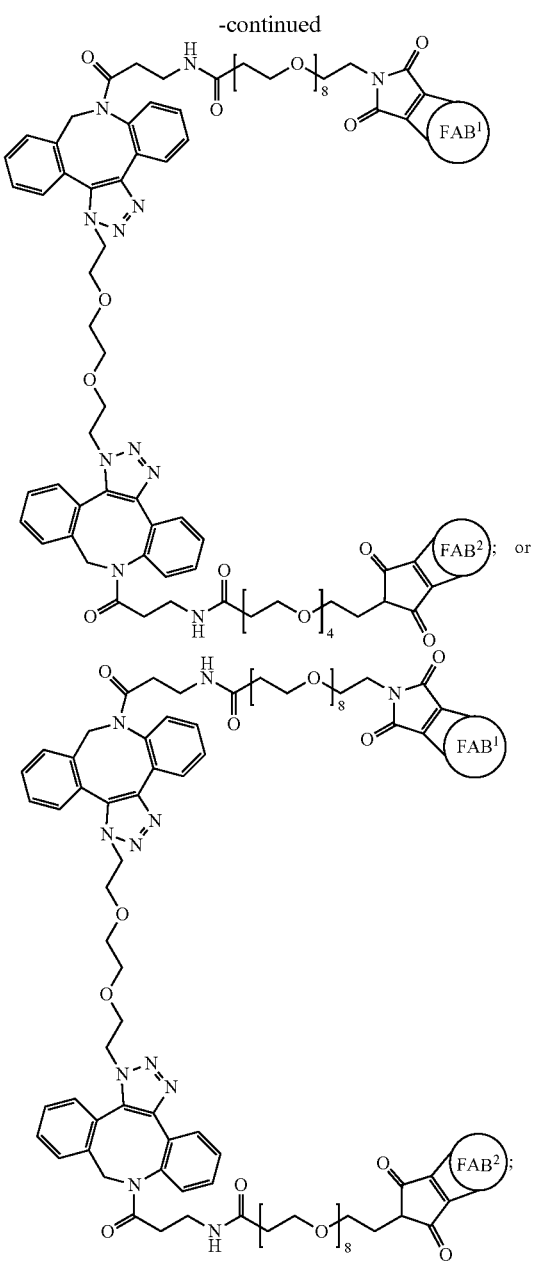

or a pharmaceutically acceptable salt thereof, wherein FAB$^1$ and FAB$^2$ are connected to the pyrrolidine-dione through native cysteine residues.

In a fourteenth embodiment, FAB$^1$ and FAB$^2$ in any one of the bispecific antibody compounds described herein are each independently selected from a Fab fragment comprising a CD3 binding region and a Fab fragment comprising a PSMA binding region.

The bispecific antibody compounds described herein can be readily prepared according to the following reaction schemes and examples, or modifications thereof, using readily available starting materials, reagents and conventional synthesis procedures. In addition, one can refer to the following references for suitable methods of synthesis as described in March, Advanced Organic Chemistry, 3rd edition, John Wiley & Sons, 1985, Greene and Wuts, Protective Groups in Organic Synthesis, 2$^{nd}$ edition, John Wiley & Sons, 1991, and Richard Larock, Comprehensive Organic Transformations, 4$^{th}$ edition, VCH publishers Inc., 1989

Bispecific antibody compounds of Formula I may be prepared according to the general reaction scheme shown in FIG. 1. In a first process, the Fc fragment along with hinge region of full length FAB is removed via digestion, as described, for example, in FIG. 1 (such as papain digestion). FAB$^1$ and FAB$^2$ are then selectively reduced to form Fab fragments. Functional moieties, X or Y (where one X or Y is an azide (N$_3$) and the other X or Y is an alkyne) are introduced into each Fab via a cysteine-based conjugation, leading to chemically modified Fab fragments, respectively in FIG. 1. The functional moieties X and Y are preferably introduced via conjugation to cysteine residues within the constant region of each Fab fragment, i.e., the light chain CL region and heavy chain CH1 constant region.

In order to achieve the chemical linkage, cysteine residues within the CH1 of the heavy chain and the CL of the light chain are reduced. In one embodiment, native cysteines that form the interchain disulfide bonds are reduced and used to chemically modify the Fab fragment as described herein. In one embodiment, the starting antibodies may contain modifications within the heavy and light chain constant regions (CH1 and CL, respectively) where additional cysteine residues are introduced.

Two Fab fragments are then linked together through a chemical ligation between X and Y moieties, to form X-Y, which correlates to variable "—X—" in the bispecific antibody compounds of Formula I.

For example, in instances where the bispecific antibody compounds are represented by Formula II, the azide could be attached to R$^1$ and the terminal alkyne could be attached to R$^2$, where ligation would occur to form the triazolyl. See Scheme 1 below.

Scheme 1:

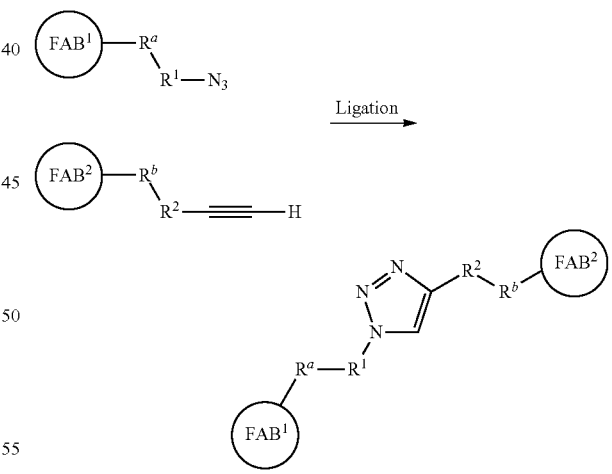

It will be understood that the reverse could also be employed where the azide is attached to R$^2$ and the terminal alkyne is on R$^1$ to form bispecific antibody compounds represented by Formula IIa.

In another example, in instances where the bispecific antibody compounds are represented by Formula III, the azide could be attached to R$^1$ and the alkyne could be attached to R$^2$, where ligation would occur to form the triazolyl. See Scheme 2 below.

Scheme 2:

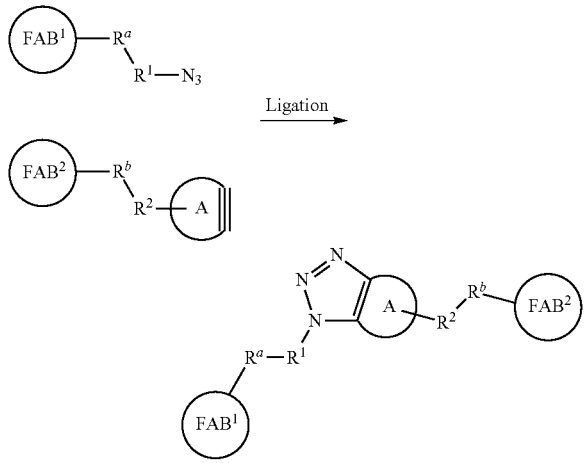

It will be understood that the reverse could also be employed where the azide is attached to $R^2$ and the alkyne is on $R^1$ to form bispecific antibody compounds represented by Formula IIIa.

In one aspect, the $FAB^1$ and $FAB^2$ are each capable of binding two different epitopes on the same or on different antigens. In one embodiment, $FAB^1$ and $FAB^2$ bind to two different epitopes on the same antigen. In one embodiment, $FAB^1$ and $FAB^2$ bind to two different antigens.

In one embodiment, $FAB^1$ and $FAB^2$ are each independently IgG1 or IgG4 isotypes. In one embodiment, $FAB^1$ and $FAB^2$ are each IgG1 isotypes. In one embodiment, $FAB^1$ and $FAB^2$ are each IgG4 isotypes. In one embodiment, $FAB^1$ is an IgG1 isotype and $FAB^2$ is an IgG4 isotype. In another embodiment, $FAB^2$ is an IgG1 isotype and $FAB^1$ is an IgG4 isotype. In one embodiment, the bispecific antibody compounds described herein bind to a target molecule selected from the group consisting of CD3, PSMA, CD19, CXCR5, CD33, PDL1, VEGFR2, cMet, and Axl. In one embodiment, the bispecific antibody compounds described herein bind to a pair of antigens selected from the following group: CD3-PSMA, CD3-CD19, CD3-CXCR5, CD3-CD33, PDL1-VEGFR2, PDL1-cMet, PDL1-Axl.

In one embodiment, the bispecific antibody compounds described herein bind to two epitopes on CD3 or binds to CD3 and another target molecule. In one embodiment, the bispecific antibody compounds described herein comprise a CD3 binding region corresponding to the CD3 binding portion, e.g., a Fab fragment, of BLINCYTO (Blinatumomab; Amgen). In another embodiment, the bispecific antibody compounds described herein comprise a Fab fragment corresponding to anti-CD3 antibodies HuM291, UCHT1, or OKT3). In another embodiment, the bispecific antibody compounds described herein comprise a Fab fragment corresponding to anti-CD3 antibodies comprising a heavy chain region comprising the amino acid sequence QVQLVQSGAEVKKPGASVKVSCKASGYTFISYTMHWVRQAPGQGLEWMGYINPRSGY THYNQKLKDKATLTADKSASTAYMELSSLRSEDTAVYYCARSAYYDYDGFAYWGQGT LVTVSSASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDKTHT (SEQ ID NO: 5); or an heavy chain comprising SEQ ID NO: 5 and light chain region comprising the amino acid sequence of DIQMTQSPSSLSASVGDRVTITCSASSSVSYMNWYQQKPGKAPKRLIYDTSKLASGVPSR FSGSGSGTDFTLTISSLQPEDFATYYCQQWSSNPPTFGGGTKVEIKRTVAAPSVFIFPPS DE QLKSGTASVVCLLNNFYPREAKVQWKVDNALQSGSQESVTEQDSKDSTYSLSSTLTLSK ADYEKHKVYACEVTHQGLSSPVTKSFNRGEC (SEQ ID NO: 6); or a light chain region comprising SEQ ID NO: 6.

In another embodiment, the bispecific antibody compounds described herein comprise a Fab fragment corresponding to anti-CD3 antibodies comprising a heavy chain variable region (HCVR) comprising the amino acid sequence QVQLVQSGAEVKKPGASVKVSCKASGYTFISYTMHWVRQAPGQGLEWMGYINPRSGY THYNQKLKDKATLTADKSASTAYMELSSLRSEDTAVYYCARSAYYDYDGFAYWGQGT LVTVSS (SEQ ID NO: 9); or an heavy chain comprising SEQ ID NO: 9 and light chain region comprising the amino acid sequence of DIQMTQSPSSLSASVGDRVTITCSASSSVSYMNWYQQKPGKAPKRLIYDTSKLASGVPSR FSGSGSGTDFTLTISSLQPEDFATYYCQQWSSNPPTFGGGTKVEIKRTVAAPSVFIFPPSDE QLKSGTASVVCLLNNFYPREAKVQWKVDNALQSGSQESVTEQDSKDSTYSLSSTLTLSK ADYEKHKVYACEVTHQGLSSPVTKSFNRGEC (SEQ ID NO: 6); or a light chain region comprising SEQ ID NO: 6. In another embodiment, the bispecific antibody compounds described herein comprise a Fab fragment corresponding to anti-CD3 antibodies comprising a heavy chain region comprising the amino acid sequence EVQLVESGGGLVQPGGSLRLSCAASGYSFTGYTMetNWVRQAPGKGLEWVALINPYKG VSTYNQKFKDRFTISVDKSKNTAYLQMetNSLRAEDTAVYYCAR SGYYGDSDWYFDVW GQGTLVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCDKTHT (SEQ ID NO: 7); or a heavy chain region comprising SEQ ID NO: 7 and light chain region comprising the amino acid sequence of
DIQMTQSPSSLSASVGDRVTITCRASQDIRNYLNWYQQKPGKAPKLLIYYTSR LESGVPSRFSGSGSGTDYTLTISSLQPEDFATYYCQQGNTLPWTFGQGTKVEIKRTVAAP SVFIFPPSDEQLKSGTASVVCLLNNFYPREAKVQWKVDNALQSGNSQESVTEQDSKDST YSLSSTLTLSKADYEKHKVYACEVTHQGLSSPVTKSFNRGEC (SEQ ID NO: 8). In another embodiment, the bispecific antibody compounds described herein comprise a Fab fragment corresponding to anti-CD3 antibodies comprising a heavy chain variable region comprising the amino acid sequence EVQLVESGGGLVQPGGSLRLSCAASGYSFTGYTMetNWVRQAPGKGLEWVALINPYKG VSTYNQKFKDRFTISVDKSKNTAYLQMetNSLRAEDTAVYYCARSGYYGDSDWYFDVW GQGTLVTVSS (SEQ ID NO: 10); or an HCVR comprising SEQ ID NO: 10 and light chain region comprising the amino acid sequence of DIQMTQSPSSLSASVGDRVTITCRASQURNYLNWYQQKPGKAPKLLIYYTSRLESGVPS RFSGSGSGTDYTLTISSLQPEDFATYYCQQGNTLPWTFGQGTKVEIKRTVAAPSVFIFPPS DEQLKSGTASVVCLLNNFYPREAKVQWKVDNALQSGNSQESVTEQDSKDSTYSLSSTL TLSKADYEKHKVYACEVTHQGLSSPVTKSFNRGEC (SEQ ID NO: 8).

In one embodiment, the bispecific antibody compounds described herein bind to two epitopes on prostate specific membrane antigen protein (PSMA) or binds to PSMA and another target molecule. In one embodiment, the bispecific antibody compounds described herein comprise a Fab fragment corresponding to antibodies 3D8, 4D4, and/or 3E11, which are described in US 2007/0031438, the contents of which are incorporated by reference herein.

In one embodiment, the bispecific antibody compounds described herein bind to two epitopes on CD19 or binds to CD19 and another target molecule. In one embodiment, the bispecific antibody compounds described herein comprise a CD19 binding region corresponding to the CD3 binding portion, e.g., a Fab fragment, of BLINCYTO (Blinatumomab; Amgen).

In one embodiment, the bispecific antibody compounds described herein bind to two epitopes on CXCR5 or binds to CXCR5 and another target molecule. In one embodiment, the bispecific antibody compounds described herein comprises a Fab fragment(s) corresponding to anti-CXCR5 antibodies which are described in U.S. patent application Ser. No. 14/825,144 filed on Aug. 12, 2015, the contents of which are incorporated by reference herein.

In one embodiment, the bispecific antibody compounds described herein bind to two epitopes on CD33 or binds to CD33 and another target molecule.

In one embodiment, the bispecific antibody compounds described herein bind to two epitopes on PDL1 or binds to PDL1 and another target molecule. In one embodiment, the bispecific antibody compounds described herein comprise a Fab fragment corresponding to anti-PDL-1 antibodies which are described in US 2013/0323249 and WO 2013/181634, the contents of which are each incorporated by reference herein. In one embodiment, the bispecific antibody compounds described herein comprise amino acid sequences corresponding to the Fab fragment of anti-PDL-1 antibody H6B1L, as described in US 2013/0323249, the contents of which are incorporated by reference herein.

In one embodiment, the bispecific antibody compounds described herein comprise a Fab fragment corresponding to anti-PDL-1 antibodies comprising a heavy chain variable region comprising the amino acid sequence of QMQLVQSGAEVKKPGSSVKVSCKASGGTFSSYAYSWVRQ APGQGLEWMGGIIPSFGTA NYAQKFQGRVTITADESTSTAYMELSSLRSEDTAVYYCARGPIVATITPLDYWGQGTLV TVSS (SEQ ID NO: 1), or a HCVR comprising the CDR sequences described in SEQ ID NO: 1, and a light chain variable region comprising the amino acid sequence of SYELMQPPSVSVAPGKTATIACGGENIGRKTVHWYQQKPGQAPVLVIYYDSDRPSGIPE RFSGSNSGNTATLTISRVEAGDEADYYCLVWDSSSDHRIFGGGTKLTVL (SEQ ID NO: 2), or a LCVR comprising the CDR sequences described in SEQ ID NO: 2.

In one embodiment, the bispecific antibody compounds described herein binds to two epitopes on VEGFR2 or binds to VEGFR2 and another target molecule. In one embodiment, the bispecific antibody compounds described herein comprises a Fab fragment corresponding to anti-VEGFR2 antibodies which are described in US 2014/0294827 and WO 2013/149249, the contents of which are each incorporated by reference herein. In one embodiment, the bispecific antibody compounds described herein comprise amino acid sequences corresponding to the Fab fragment of anti-VEGFR2 antibody VK-B8, as described in US 2014/0294827, the contents of which are incorporated by reference herein.

In one embodiment, the bispecific antibody compounds described herein comprise a Fab fragment corresponding to anti-VEGFR2 antibodies comprising a heavy chain variable region comprising the amino acid sequence of MAQVQLVQSGAEVKKPGSSVKVSCKAYGGTFGSYGVSWVRRAPGQGLEWMGRLIPIF GTRDYAQKFQGRVTLTADESTNTAYMELSSLRSEDTAVYYCARDGDYYGSGSYYGMD VWGQGTLVTVSS (SEQ ID NO: 3), or a HCVR comprising the CDR sequences described in SEQ ID NO: 3, and a light chain variable region comprising the amino acid sequence of ETTLTQSPATLSVSPGERATVSCRASQSLGSNLGWFQQKPGQAPRLLIYGASTRATGIPA RFSGSGSGTEFTLTISSLQSEDFAVYFCQQYNDWPITFGQGTRLEIK (SEQ ID NO: 4), or a LCVR comprising the CDR sequences described in SEQ ID NO: 4.

In one embodiment, the bispecific antibody compounds described herein bind to two epitopes on cMet or binds to cMet and another target molecule. In one embodiment, the bispecific antibody compounds described herein comprise a Fab fragment corresponding to anti-cMet antibodies which are described in U.S. patent application Ser. No. 13/924492 and PCT WO 2013/192594 , the contents of which are incorporated by reference herein.

In one embodiment, the bispecific antibody compounds described herein binds to two epitopes on Axl or binds to Axl and another target molecule.

Fab fragments used in the bispecific antibody compounds described herein may be made using standard recombinant methods known in the art. In one embodiment, full length antibodies (i.e., an antibody comprising a Fab region, a hinge region and an Fc region) are produced and subsequently digested to provide Fab fragments for use in the bispecific antibody compounds described herein. Alternatively, Fab fragments are produced in host cells, which eliminates the need to digest a full length antibody.

Production methods described herein are applicable to full length antibodies and fragments thereof, including Fab fragments.

Recombinant antibody production is known in the art. For example, for recombinant production of an antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

In one embodiment, an antibody is produced using prokaryotic cells. Sequences encoding the polypeptides are inserted into a recombinant vector capable of replicating and expressing heterologous polynucleotides in prokaryotic hosts. Many vectors that are available and known in the art can be used. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

Prokaryotic host cells suitable for expressing antibodies include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. coli* cells are used as hosts. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 fhuA (tonA) ptr3 lac Iq lacL8 ompT (nmpc-fepE) degP41 kan.sup.R (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia,* or *Salmonella* species can be suitably used as the host when well-known plasmids such as pBR322, pBR325, pACYC177, or pKN410 are used to supply the replicon.

Prokaryotic host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the bispecific antibody compounds described herein are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

The expressed antibody proteins described herein are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

Antibodies may also be produced in eukaryotic host cells. For eukaryotic expression, the vector components are known in the art and generally include, but are not limited to, one or more of the following, a signal sequence, an origin of replication, one or more marker genes, and enhancer element, a promoter, and a transcription termination sequence.

Eukaryotic host cells are transformed with expression or cloning vectors for antibody production and cultured in conventional nutrient media modified as appropriate for inducing promoters, selecting transformants, or amplifying the genes encoding the desired sequences. Suitable host cells for cloning or expressing the DNA in the vectors (i.e., DNA encoding an antibody) include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

The host cells used to produce the antibodies described herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or U.S. Pat. No. 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

One produced, the antibody produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one embodiment, Protein A may be used to purify a full length antibody prior to digestion to obtain Fab fragments used in the bispecific antibody compounds of Formula I. The suitability of Protein A as an affinity ligand depends on the species and isotype of any immunoglobulin Fc domain that is present in the antibody. Protein A can be used to purify antibodies that are based on human immunoglobulins containing 1, 2, or 4 heavy chains (Lindmark et al., J. Immunol. Meth. 62:1-13 (1983)). Protein G is recommended for all mouse isotypes and for human 3 (Guss et al., EMBO J. 5:15671575 (1986)).

In one aspect, Protein A immobilized on a solid phase is used for immunoaffinity purification of the full length antibody products. Protein A is a 41 kD cell wall protein from *Staphylococcus* aureas which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants. The solid phase is then washed to remove contaminants non-specifically bound to the solid phase. Finally the antibody of interest is recovered from the solid phase by elution.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

Antibodies may be identified using any number of techniques known in the art. Preferably, the antibody is a monoclonal antibody. Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. For example, the monoclonal antibodies may be made using the hybridoma method first described by Kohler et al., Nature, 256:495 (1975), or may be made by recombinant DNA methods (U.S. Pat. No. 4,816,567).

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., Curr. Opinion in Immunol., 5:256-262 (1993) and Pluckthun, Immunol. Revs. 130:151-188 (1992).

In a further embodiment, antibodies can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nucl. Acids Res., 21:2265-2266 (1993)). Thus, these techniques are viable alternatives to traditional monoclonal antibody hybridoma techniques for isolation of monoclonal antibodies.

In certain embodiment, the antibodies described herein may be humanized or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementarity determining region (CDR) (HVR as used herein) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domain, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Jones et al., Nature 321: 522-525 (1986); Riechmann et al., Nature 332: 323-329 (1988) and Presta, Curr. Opin. Struct. Biol. 2: 593-596 (1992).

Recombinant human antibodies can be generated using methods known in the art. For example, transgenic animals (e.g., mice) may be produced that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); U.S. Pat. No. 5,591,669 and WO 97/17852.

Alternatively, phage display technology can be used to produce human antibodies and antibody fragments in vitro, from immunoglobulin variable (V) domain gene repertoires from unimmunized donors. McCafferty et al., Nature 348: 552-553 (1990); Hoogenboom and Winter, J. Mol. Biol. 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Curr. Opin Struct. Biol. 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also, U.S. Pat. Nos. 5,565,332 and 5,573,905.

The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., J. Immunol. 147(1): 86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., Bio/Technology 10: 779-783 (1992); Lonberg et al., Nature 368: 856-859 (1994); Morrison, Nature 368: 812-13 (1994), Fishwild et al., Nature Biotechnology 14: 845-51 (1996), Neuberger, Nature Biotechnology 14: 826 (1996) and Lonberg and Huszar, Intern. Rev. Immunol. 13: 65-93 (1995). Finally, human antibodies may also be generated in vitro by activated B cells (see U.S. Pat. Nos. 5,567,610 and 5,229,275).

Specific examples of the bispecific antibody compounds are provided in the EXEMPLIFICATION. Pharmaceutically acceptable salts as well as the neutral forms of these bispecific antibody compounds are included herein.

In certain embodiments, the present disclosure provides a method of treating a patient (e.g., a human) with a disorder mediated by a therapeutic target, e.g., CD3, PSMA, CD19, CXCR5, CD33, PDL1, VEGFR2, cMet, and Axl, comprising the step of administering to the patient an effective amount of the bispecific antibody compound as described herein, or a composition thereof.

Formulation and Administration

In certain embodiments, the present disclosure provides a method of treating a subject (e.g., a human) with a disorder mediated by a therapeutic target (target molecule(s)), e.g., CD3, PSMA, CD19, CXCR5, CD33, PDL1, VEGFR2, cMet, and Axl, using a composition comprising a bispecific antibody compound described herein and a pharmaceutically acceptable carrier. In certain embodiments, the amount of bispecific antibody compound described herein in a provided composition is such that it is effective as an inhibitor or agonist in a biological sample or in a subject. In certain embodiments, a provided composition is formulated for administration to a subject in need of such composition. In some embodiments, a provided composition is formulated for parenteral or intravenous administration to a subject.

The term "pharmaceutically acceptable carrier" refers to a non-toxic carrier, adjuvant, or vehicle that does not destroy the pharmacological activity of the antibody with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided bispecific antibody compound in the composition will also depend upon the particular compound in the composition.

Uses of Bispecific Antibody Compounds

Bispecific antibody compounds and compositions described herein are generally useful for modulating molecules to which the antibodies are specific. Examples of molecules which may be bound by the bispecific antibody compounds described herein include, but are not limited to, CD3, PSMA, CD19, CXCR5, CD33, PDL1, VEGFR2, cMet, and Axl, including combinations thereof. In one embodiment, the bispecific antibody compounds described herein bind a pair of antigens selected from the following combinations: CD3-PSMA, CD3-CD19, CD3-CXCR5, CD3-CD33, PDL1-VEGFR2, PDL1-cMet, and PDL1-Axl.

Thus, in some embodiments, the present disclosure provides a method of treating disorders associated with detrimental activity of CD3, PSMA, CD19, CXCR5, CD33, PDL1, VEGFR2, cMet, or Axl, comprising administering a provided compound or composition.

In one embodiment, the bispecific antibody compounds described herein bind an antigen or combination of antigens selected from the following: CD3, PSMA, CD19, CXCR5, CD33, PDL1, VEGFR2, cMet, and Axl, may be used to treat a subject having a disorder selected from non-Hodgkin lymphoma (NHL), prostate cancer, B-cell lymphoma, acute myeloid leukemia (AML), colon cancer, breast cancer. Modulation of a target molecule(s), e.g., CD3, PSMA, CD19, CXCR5, CD33, PDL1, VEGFR2, cMet, and/or Axl, of the bispecific antibody compound described herein means that a change or alternation in the activity of the target molecule(s), e.g., CD3, PSMA, CD19, CXCR5, CD33, PDL1, VEGFR2, cMet, and/or Axl, has occurred from the administration of one or more of the bispecific antibody compounds described herein. Modulation may be an upregulation (increase) or a downregulation (decrease) in the magnitude of the activity or function of the target molecule(s), e.g., CD3, PSMA, CD19, CXCR5, CD33, PDL1, VEGFR2, cMet, and Axl. Exemplary activities and functions include e.g., binding characteristics, enzymatic activity, cell receptor activation, transcriptional activity, and signal transduction.

Diseases and conditions treatable according to the methods using the bispecific antibody compounds described herein include, but are not limited to, treating or ameliorating cancer or another proliferative disorder by administration of an effective amount of a bispecific antibody compound described herein to a mammal, e.g., a human in need of such treatment. In some aspects, the disease and conditions to be treated by the methods herein is cancer. Examples of cancers treated using the compounds and methods described herein include, but are not limited to, adrenal cancer, acinic cell carcinoma, acoustic neuroma, acral lentigious melanoma, acute eosinophilic leukemia, acute erythroid leukemia, acute lymphoblastic leukemia, acute megakaryoblastic leukemia, acute monocytic leukemia, actue promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In one aspect the diseases and conditions treatable by the according to the methods using the bispecific antibody compounds described herein are selected from non-Hodgkin lymphoma (NHL), prostate cancer, B-cell lymphoma, acite myeloid leukemia (AML), colon cancer, and breast cancer. In one embodiment, the bispecific antibody compounds described herein are used as bispecific T cell engagers, and are able to exert action on its antigen selectively and direct the human immune system to act against a tumor cell.

In one embodiment, a human patient is treated with a bispecific antibody compounds described herein and a pharmaceutically acceptable carrier, adjuvant, or vehicle, wherein said bispecific antibody compound is present in an amount to treat or ameliorate one or more of the diseases and conditions recited above. In an alternative embodiment, the diseases and conditions treated or ameliorated by a bispecific antibody compound described herein include, any one of those described above. In one aspect, the diseases and conditions are selected from non-Hodgkin lymphoma (NHL), prostate cancer, B-cell lymphoma, acite myeloid leukemia (AML), colon cancer, breast cancer, in the patient.

EXEMPLIFICATION

As depicted in the Examples below, in certain exemplary embodiments, bispecific antibody compounds are prepared according to the following general procedures. It will be appreciated that, although the general methods depict the synthesis of certain compounds herein, the following general methods, and other methods known to one of ordinary skill in the art, can be applied to all bispecific antibody compounds and subclasses and species of each of these bispecific antibody compounds, as described herein.

Preparation of Bispecific Antibodies Compounds of Formula I

Fc and Hinge Region Removal of Antibodies

Antibodies were buffered exchange into 20 mM Sodium Phosphate (JT Baker 3827-01) and 10 mM EDTA (Aldrich E26290) and (1.0 mg) was added to 80 µL Papain Slurry (Thermo Scientific Pierce 20341) with 20 mM Cysteine (Sigma C7352) and incubated in 37° C. for 6.5 h in head to head spinner. Fc fragment and undigested IgG was then removed from the Fab using protein A purification via ÄKTA pure chromatography system.

Figure 5:
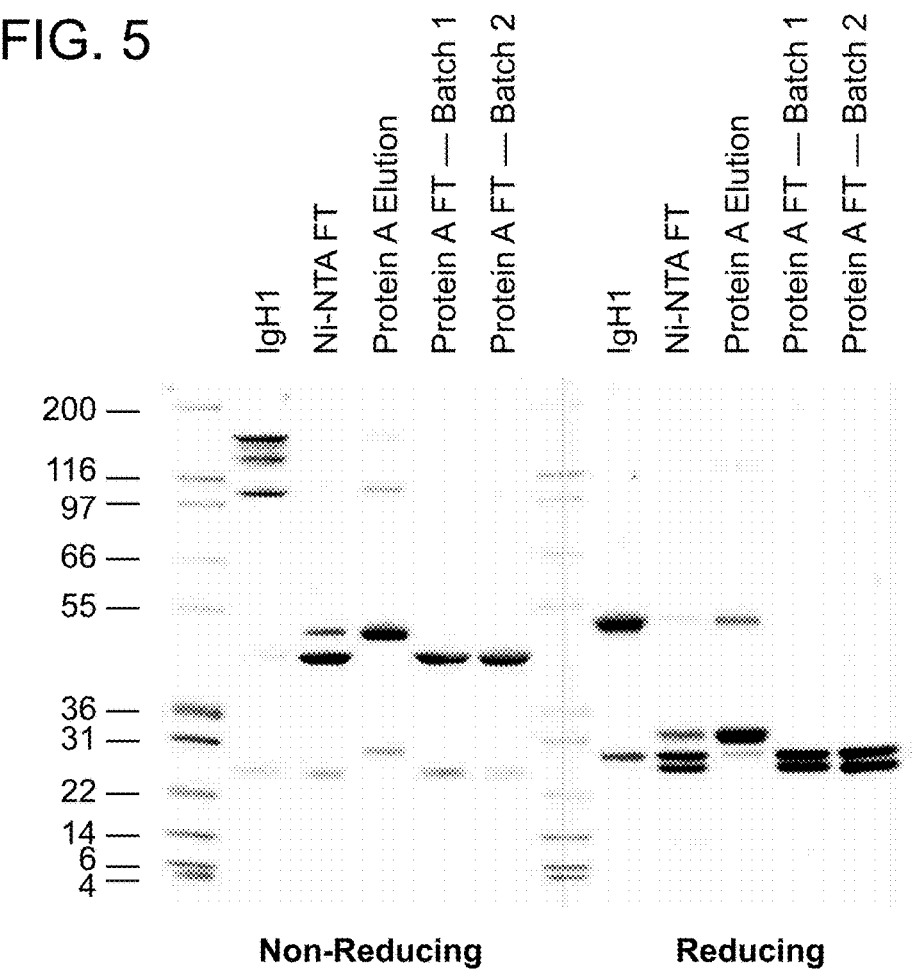
FIG. 5 illustrates the SDS-PAGE analysis following digestion and purification from full length IgG1 antibody.
Figure 6:
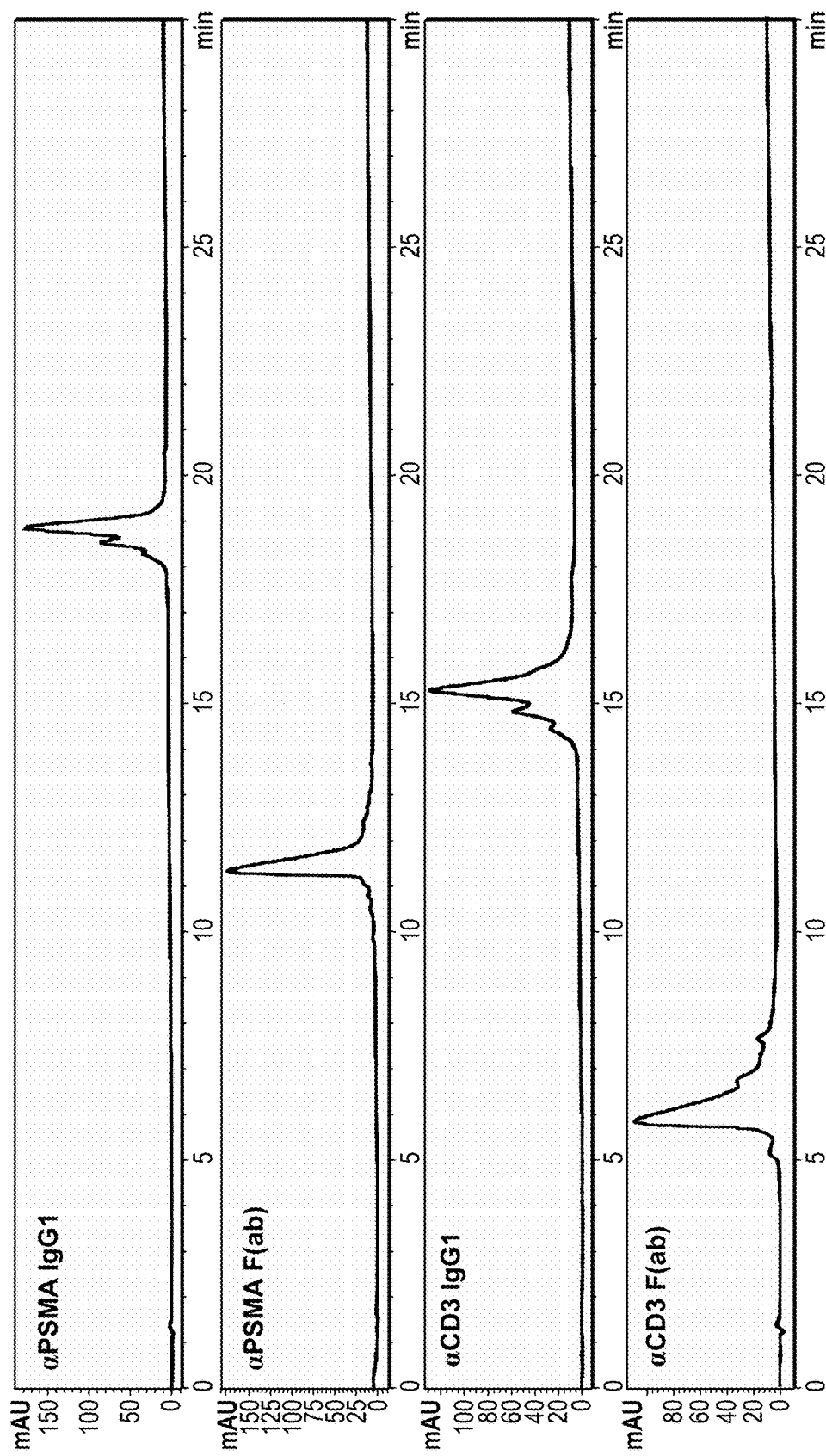
FIG. 6 illustrates a Hydrophobic Interaction Chromatography (HIC) analysis of PSMA F(ab) and CD3 F(ab) following digestion and purification from full length PSMA IgG1 and full length CD3 IgG1.

In an alternative, proteolytic digestion of IgG1 allowed generation of F(ab) proteins. SpeB cysteine protease, FabULOUS (Genovis), was used to digest the hinge region of IgG1 to produce F(ab) and Fc fragments. A digestion procedure was adopted using 0.1-0.2 U/µg overnight (~16 h) at 37° C. in Dulbecco's phosphate-buffered saline (DPBS) with 1 mM dithiothreitol (DTT). Samples were then either buffer exchanged to remove DTT or diluted to decrease DTT concentration prior to F(ab) purification. Protease was removed by Ni-NTA gravity column, then the flow-through (FT) was subjected to Protein A purification by standard methods. Protein A FT contain the F(ab) fragment while the Fc and any undigested IgG1 was retained in the column. For larger scale F(ab) preparations, digestion was performed in a buffer containing 20 mM imidazole, 0.5 M NaCl, and 20 mM sodium phosphate (pH 7.4) with 0.1 mM DTT using 0.1-0.2 U/µg overnight (~16 h) at 37° C. enabling tandem HisTrap FF (GE) and HiTrap MabSelect SuRe (GE) purification on an ÄKTA pure chromatography system. F(ab) purity was assessed by SDS-PAGE analysis and HIC HPLC. See FIG. 5 and FIG. 6.

SDS-PAGE Analysis

Sodium dodecyl sulfate polyacrylamide gel electrophoresis (SDS-PAGE) was employed using NuPAGE Novex 4-12% Bis-Tris Protein Gels with NuPAGE MOPS SDS Running Buffer in a XCell SureLock Mini electrophoresis system. All samples (2.5 µg) included NuPAGE LDS Sample Buffer and were heated to 95° C. for 5 min prior to loading. Reduced samples also contained NuPAGE Sample Reducing Agent. Mark12 Unstained Standard (10 µL) was used for estimation of molecular weights. After gel electrophoresis at 125 V for 1.5 h, gels were fixed for 5 min and stained with SYPRO Ruby Protein Gel Stain following the recommended procedures. Imaging was performed with a Bio-Rad ChemiDoc MP System and analyzed by Image Lab Software.

SDS-PAGE Analysis Hydrophobic Interaction Chromatography (HIC) HPLC

Analysis by HIC HPLC used a TOSOH TSKgel Butyl-NPR (4.6 mm ID×10 cm, 2.5 µm) column at 40° C. on an Agilent 1260 Infinity system. Analytical runs were performed using 50 µg sample with a linear gradient of 0-60%B over 30 min: A=50 mM sodium phosphate+1 M ammonium sulfate (pH 7), B=50 mM sodium phosphate+25% isopropanol (pH 7). All data was analyzed using OpenLAB Software.

General Procedure for Cyclization

Figure 7:
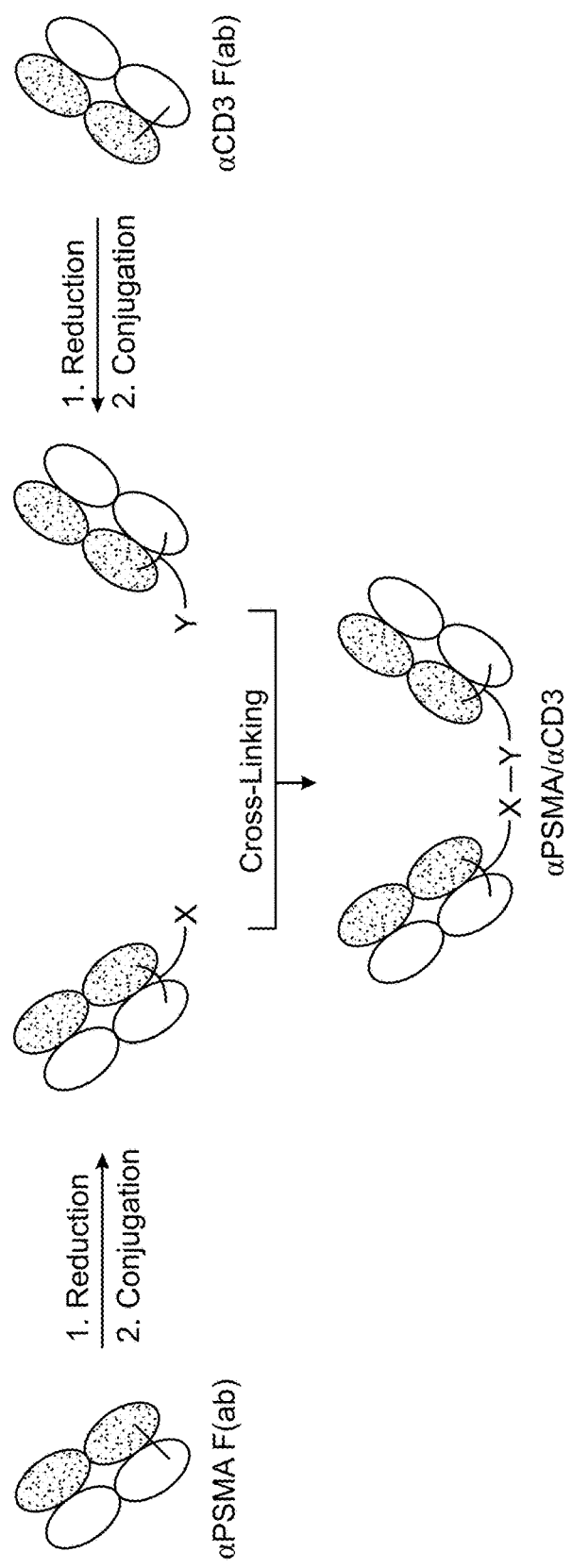
FIG. 7 shows a general synthetic scheme for the formation of PSMA/CD3 bispecific antibody compounds 106, 107, 108, and 109.
Figure 8:
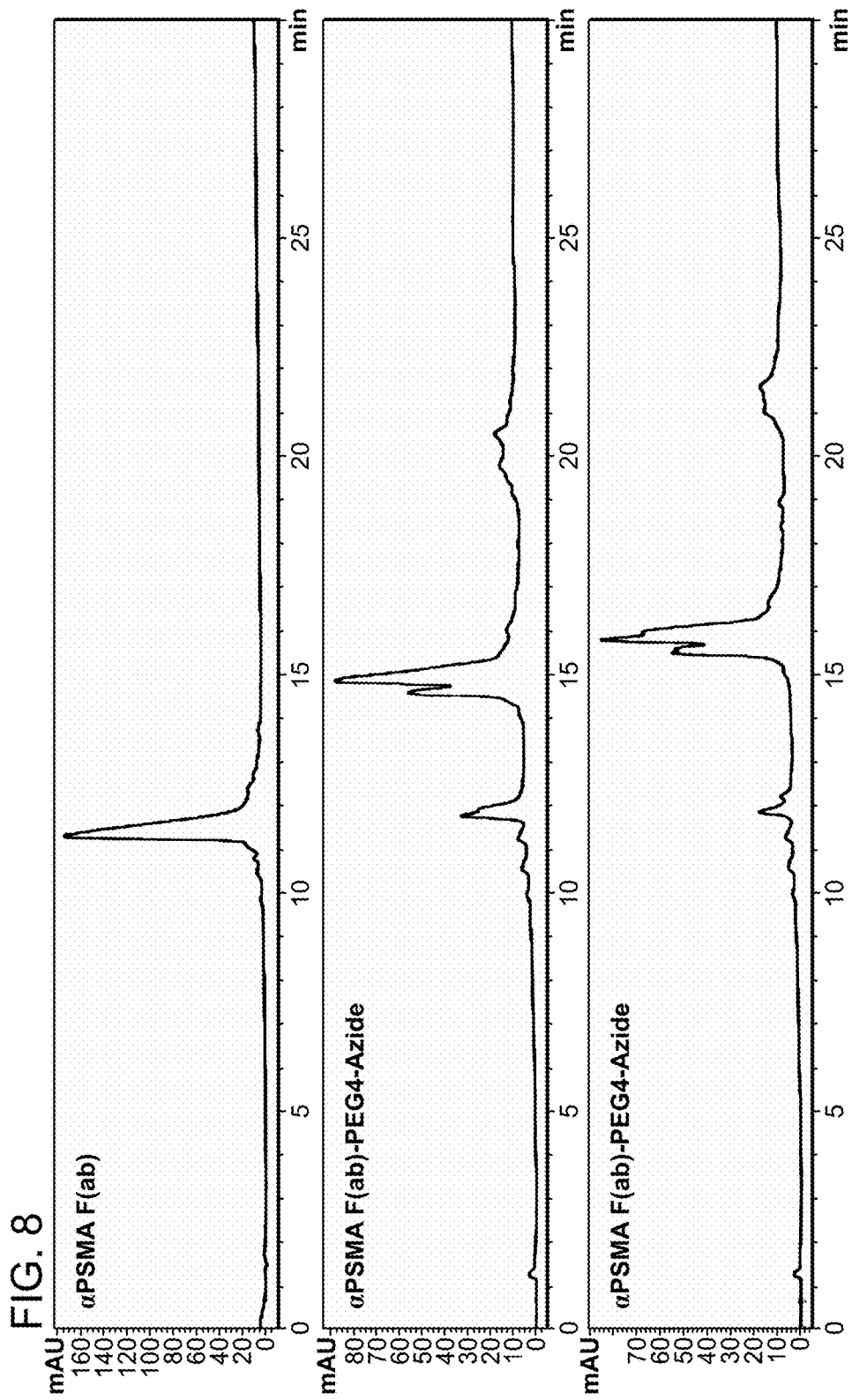
FIG. 8 shows the HIC analysis of aPSMA F(ab) and intermediates aPSMA F(ab)-PEG4-azide and aPSMA F(ab)-PEG8-azide prior to cyclization.
Figure 9:
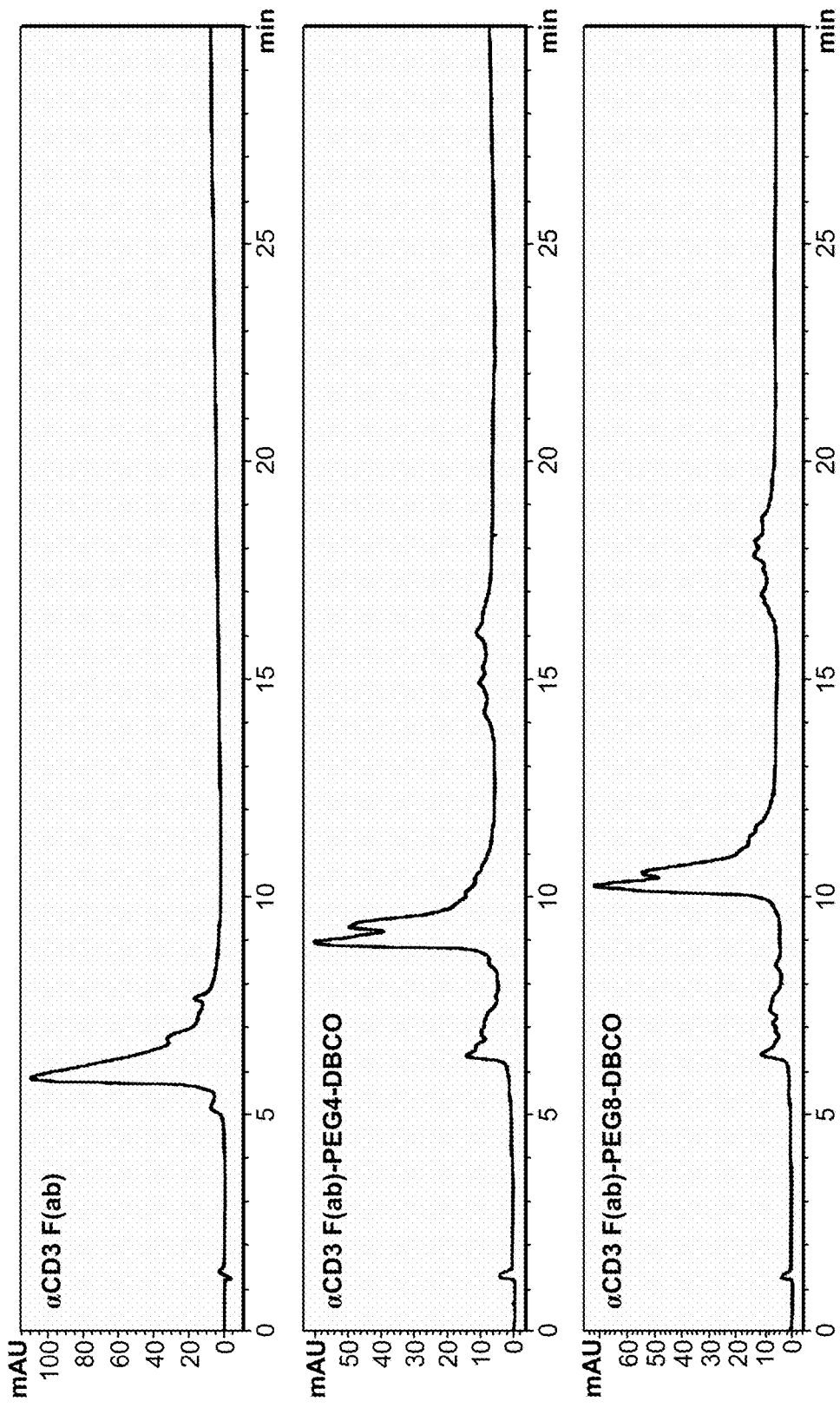
FIG. 9 shows the HIC analysis of aCD3 F(ab) and intermediates αCD3 F(ab)-PEG4-DBCO and αCD3 F(ab)-PEG8-DBCO prior to cyclization.

Conjugation of $FAB^1$ and $FAB^2$ was enabled through reduction of the interchain disulfide bonds, followed by reaction with a 2,3-dibromomaleimide (DBM) intermediate comprising an azide or dibenzylcyclooctyne (DBCO). Cyclization was then commenced via copper-free click chemistry. See also FIG. 7 for a general representation of the approach using αPSMA and αCD3 as an example. The 2,3-dibromomaleimide (DBM) intermediates comprising an azide were prepared in situ by reacting the appropriate DBM-PEG-DBCO linker (e.g., for αPSMA/αCD3 bispecific antibody compounds described below, DBM-PEG4-DBCO and DBM-PEG8-DBCO were used) with 10-15 equivalents of the appropriate azido-PEG-azide (e.g., for αPSMA/αCD3 bispecific antibody compounds described below, azido-PEG2-azide was used) for 1 h at room temperature (RT). F(ab) proteins (e.g., αPSMA, αCD3) at 5 mg/mL were typically reduced using 5 or 10 equivalents of DTT for 1 hour at RT followed by conjugation with 10 or 15 equivalents DBM linker, respectively, and 7.5% DMSO co-solvent overnight at RT. Excess linker was removed by centrifugal filtration. Heavy chain-light chain disulfide bridging was determined to be ~85% efficient by SDS-PAGE and HIC HPLC analysis. Cyclization was initiated by mixing the FAB$^1$-X intermediate and the FAB$^2$-Y intermediate at 5 mg/mL for 24-48 h at either room temperature or 37° C. Purity of the antibody and intermediates prior to cyclization was assessed by SDS-PAGE analysis and HIC HPLC. See FIG. 6, FIG. 8, and FIG. 9 for data pertaining to the αCD3 F(ab) and αPSMA F(ab) products. Cyclization products were usually formed with ~65-95% yield depending on incubation temperature and time.

Anti-PDL1/Anti-VEGFR2 Bispecific Antibody Compounds

A bispecific antibody compound of Formula I, where FAB$^1$ is anti-PDL1 and FAB$^2$ is anti-VEGFR2 was prepared as follows. The FAB$^1$ (anti-PDL1 antibody) comprised variable regions having amino acid sequences corresponding to SEQ ID Nos: 1 and 2. The FAB$^2$ (anti-VEGFR2 antibody) comprised variable regions having amino acid sequences corresponding to SEQ ID Nos: 3 and 4.

Following Fc removal of anti-PDL1 and anti-VEGFR2, each antibody (1-10 mg) was added to separate 15 mL filter centrifuge tubes (Millipore, UFC903024) and an appropriate volume of a 50 mM sodium phosphate, 150 mM NaCl, 5 mM EDTA, pH 7.7 buffer was added to the 50 mL mark on the tube. The tubes were centrifuged at 3,000 RPM for 20 min at 22° C. The antibodies were then transferred into separate 1.5 mL plastic vials and concentrations were confirmed using Nanodrop (Fisher, ND-2000 UV-Vis Spectrophotometer). The final antibody concentrations were up to 5 mg/mL. In this example, anti-PDL1 was used as FAB$^1$ and anti-VEGFR2 was used as FAB$^2$.

A stock solution of 1 mg/mL TCEP ((tris(2-carboxyethyl) phosphine)), Sigma-Aldrich, C4706) in pH 8.0 PBS (1 mM EDTA) buffer was prepared. Five equivalents of TCEP was added to FAB$^1$ and the mixture was shaken and incubated at room temperature for 1 h. TCEP was separated from the reduced FAB$^1$ using a NAP-5 (GE17-0853-02) desalting column.

A stock solution of Dibromo-DBCO (2,3-dibromomaleic anhydride; Click Chemistry Tools, A108-100) in DMSO (Sigma-Aldrich, 472301) was prepared and 1 equivalent of Dibromo-DBCO in DMSO was added to the FAB$^1$ sample. The final volume of DMSO in the sample was about 5-9% (v/v). The conjugation reaction between Dibromo-DBCO and FAB$^1$ was conducted for 1 h at RT under mixing by carousel. This step was repeated two more times. The final concentration for the Dibromo-DBCO was 3 equivalents of FAB$^1$.

The Dibromo-azide (1 equivalents) in DMSO was added to the FAB$^1$ sample. Final volume of DMSO in antibody sample is about 5-9% (v/v). The conjugation reaction was conducted for 1 h at RT under mixing by carousel, this step was repeated for two more times with final concentration for the Dibromo-DBCO being 3 equivalents.

Each sample was placed into a separate 15 mL filter centrifuge tube (Millipore, UFC903024) and added an appropriate volume of 1× PBS plus 10% DMSO (Corning, 21-031-CM, no calcium or magnesium) buffer to the 50 mL mark on the tube. The samples were centrifuged at 3,000 RPM for 20 min at 22° C. The wash step was repeated once more. Then an appropriate volume of 1× DPBS (Corning, 21-031-CM, no calcium or magnesium) buffer was added to the 50 mL mark on the tube. The samples were centrifuged at 3,000 RPM for 20 min at 22° C. After wash, the samples was transferred into separate 1.5 mL plastic vials and placed in refrigerator (5° C.) or was used for click step.

Figure 2:
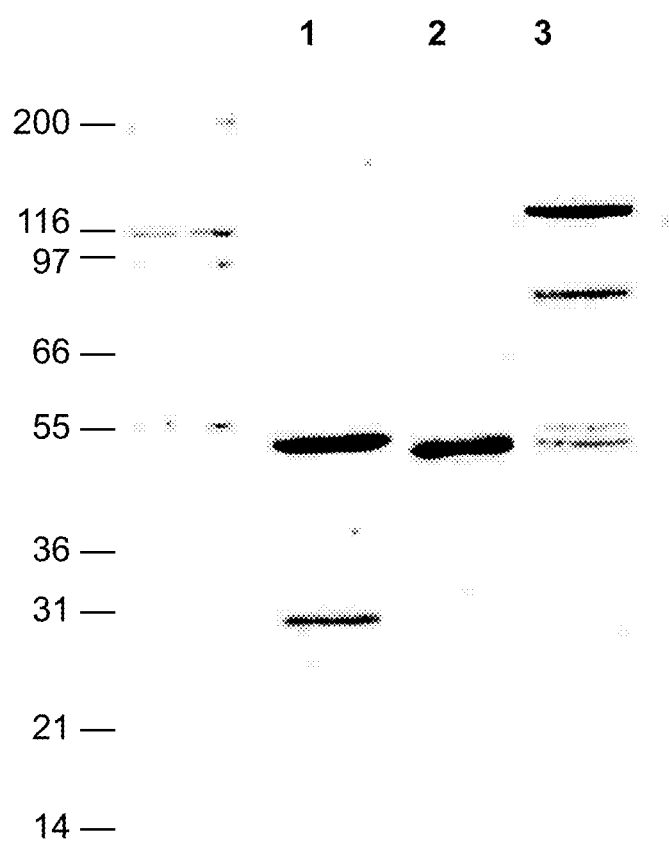
FIG. 2 illustrates an SDS-PAGE gel analysis of intermediates involved in the synthesis of an exemplary bispecific antibody.

For each sample to be analyzed, 20 μL at a concentration of 0.6 mg/mL is required. Follow the established protocols for running SDS-PAGE gels (RTP AD001-01 and AD002-01) See FIG. 2, where 1) represents FAB$^1$-DBCO; 2) represents FAB$^2$-azide; and 3) represents the bispecific antibody compound of Formula I (Click product from FAB$^1$-DBCO and FAB$^2$-azide.

Specific examples are provided below.

1-(2-(2-azidoethoxy)ethyl)-3,4-dibromo-1H-pyrrole-2,5-dione

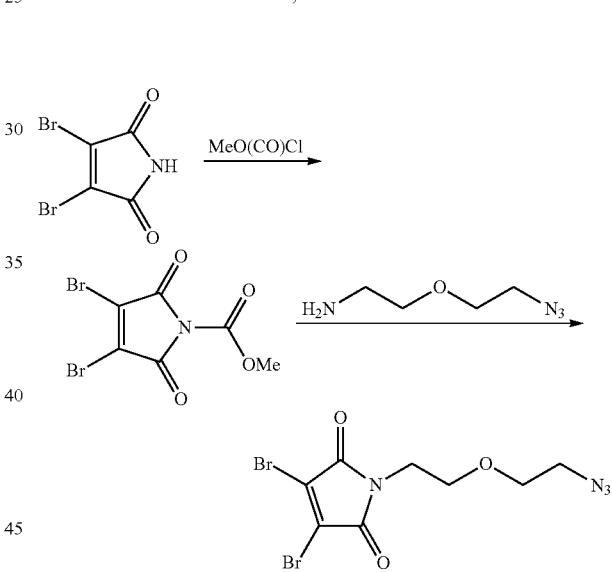

To 2.5 g of 3,4-dibromo-1H-pyrrole-2,5-dione (10 mmol) and 1 g of NMM in 60 mL of THF, MeOCOCl (10 mmol, 940 mg in 10 ml DCM) was added dropwise, stirred for 20 min, then the reaction solution was diluted with 60 mL of DCM, washed 3 time by water, the organic phase was stirred by sodium sulfate anhydrous, concentrated, 2.65 g of methyl 3,4-dibromo-2,5-dioxo-2H-pyrrole-1(5H)-carboxylate was obtained. To 311 mg, 1 mmol of this compound, 2-(2-azidoethoxy)ethanamine (130 mg, 1 mmol) and 5 mL DCM was added, TLC shown the reaction finished in 20 min, then extracted by DCM and brine, washed by NH$_4$Cl solution, dried on sodium sulfate anhydrous, and then concentrated for column purification, flashed by 2:1 hexane and ethyl ethylate, 230 mg of 1-(2-(2-azidoethoxy)ethyl)-3,4-dibromo-1H-pyrrole-2,5-dione obtained. $^1$HNMR: 3.32 ppm (t, J=5.0 Hz, 1H), 3.40 ppm (t, J=5.0 Hz, 1H), 3.50 ppm (q, J=5.0 Hz, 1H), 3.62 ppm (t, J=5.0 Hz, 1H), 3.63-3.69 ppm (m, 3H), 3.84 ppm (t, J=5 hz, 1H). Fw: 365.9, C$_8$H$_8$Br$_2$N$_4$O$_3$; Mass Peaks (1:2:1): 366.9, 368.9, 370.9.

N-(3-(1-(2-(2-(2-azidoethoxy)ethoxy)ethyl)-1,9-dihydro-8H-dibenzo[b,f][1,2,3]triazolo[4,5-d]azocin-8-yl)-3-oxopropyl)-1-(3,4-dibromo-2,5-dioxo-2,5-dihydro-1H-pyrrol-1-yl)-3,6,9,12-tetraoxapentadecan-15-amide (102)

A stock solution of Dibromo-DBCO (2,3-dibromomaleic anhydride; Click Chemistry Tools, A108-100) in DMSO (Sigma-Aldrich, 472301) was prepared and 1 equivalent of Dibromo-DBCO in DMSO was added to the FAB[1] sample. The final volume of DMSO in the antibody sample was

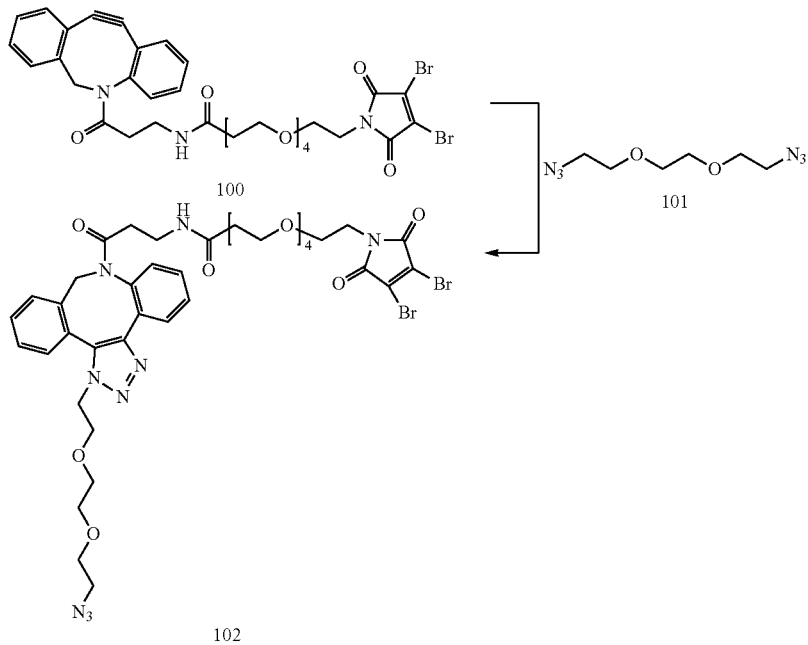

To a solution of dibromo-maleimide-PEG2-dibenzocyclooctyne (1.0 mg, 1.0 equivalent, 100) in DMSO (0.13 mL) was added azido-PEG2-azide (1.4 mg, 5.0 equivalent, 101) in DMSO (0.7 mL). The mixture was stirred at room for 1hr. The reaction was completed as indicated by LC/MS. Molecular weight of the resulting dibromo-maleimide-azide 102 was 961.1 g/mol.

Dibenzocyclooctane-PEG4-maleimide-FAB[1]

about 5-9% (v/v). The conjugation reaction was conducted for 1 hour at room temperature under mixing by carousel. This step was repeated two more times. The final concentration for the Dibromo-DBCO was 3 equivalent of FAB[1].

The sample was placed into a separate 15 mL filter centrifuge tube (Millipore, UFC903024) and added an appropriate volume of 1X DPBS plus 10% DMSO (Corning, 21-031-CM, no calcium or magnesium) buffer was added to the 50 mL mark on the tube. The sample was centrifuged at

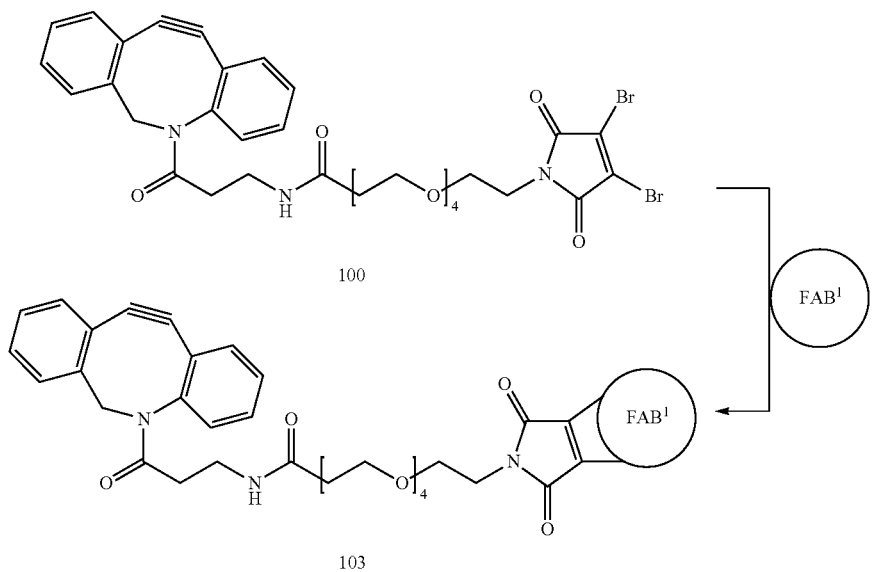

3,000 RPM for 20 minutes at 22° C. The wash step was repeated once more. Then an appropriate volume of 1× DPBS (Corning, 21-031-CM, no calcium or magnesium) buffer was added to the 50 mL mark on the tube. The sample were centrifuged at 3,000 RPM for 20 minutes at 22° C. After wash, the sample was transferred into separate 1.5 mL plastic vials and placed in refrigerator (5° C.) to afford 103.

Azido-PEG2-dibenzo[b,f][1,2,3]triazolo[4,5-d]azocin-8-yl)-3-oxopropyl)-PEG4-maleimide-FAB$^2$

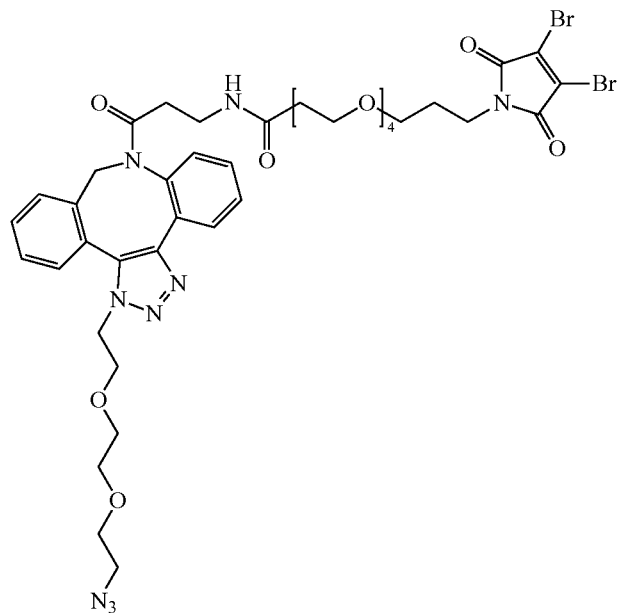

102 times. The final concentration for the Dibromo-DBCO was 3 equivalent of FAB$^2$.

The sample was placed into a separate 15 mL filter centrifuge tube (Millipore, UFC903024) and an appropriate volume of 1× DPBS plus 10% DMSO (Corning, 21-031-CM, no calcium or magnesium) buffer was added to the 50 mL mark on the tube. The sample was centrifuged at 3,000 RPM for 20 minutes at 22° C. The wash step was repeated once more. Then an appropriate volume of 1× DPBS (Corn-

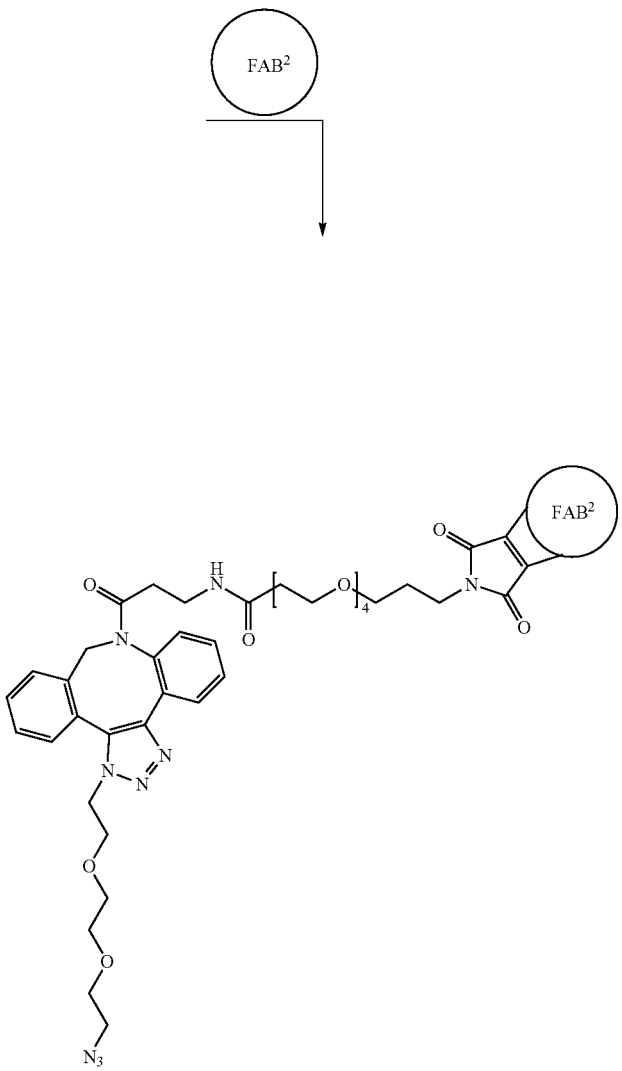

104

The Dibromo-azide 102 (1 equivalents) in DMSO was added to the FAB$^2$ sample. The final volume of DMSO in the antibody sample was about 5-9% (v/v). The conjugation reaction was conducted for 1 hour at room temperature under mixing by carousel. This step was repeated two more ing, 21-031-CM, no calcium or magnesium) buffer was added to the 50 mL mark on the tube. The sample was centrifuged at 3,000 RPM for 20 minutes at 22° C. After wash, the sample was transferred into separate 1.5 mL plastic vials and placed in refrigerator (5° C.) to afford 104.

PEG4 Anti-PDL1/PEG 4Anti-VEGFR2 Bispecific Antibody Compound

103
+
104

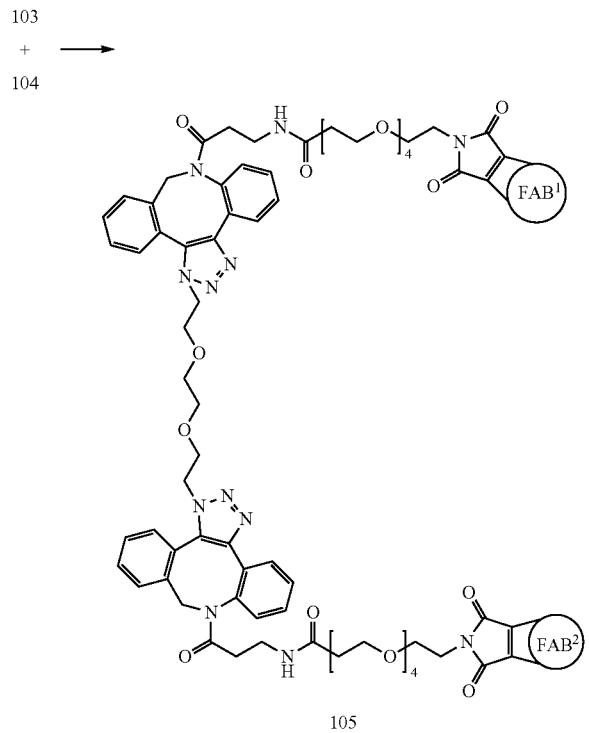

105

To 103 (500 μg) in PBS (5.0 mg/mL) was added 104 fragment (500 μg) in PBS (5.0 mg/mL). The reaction was conducted for overnight at room temperature under mixing by carousel. The mixture was subjected to SEC analysis.

Figure 3:
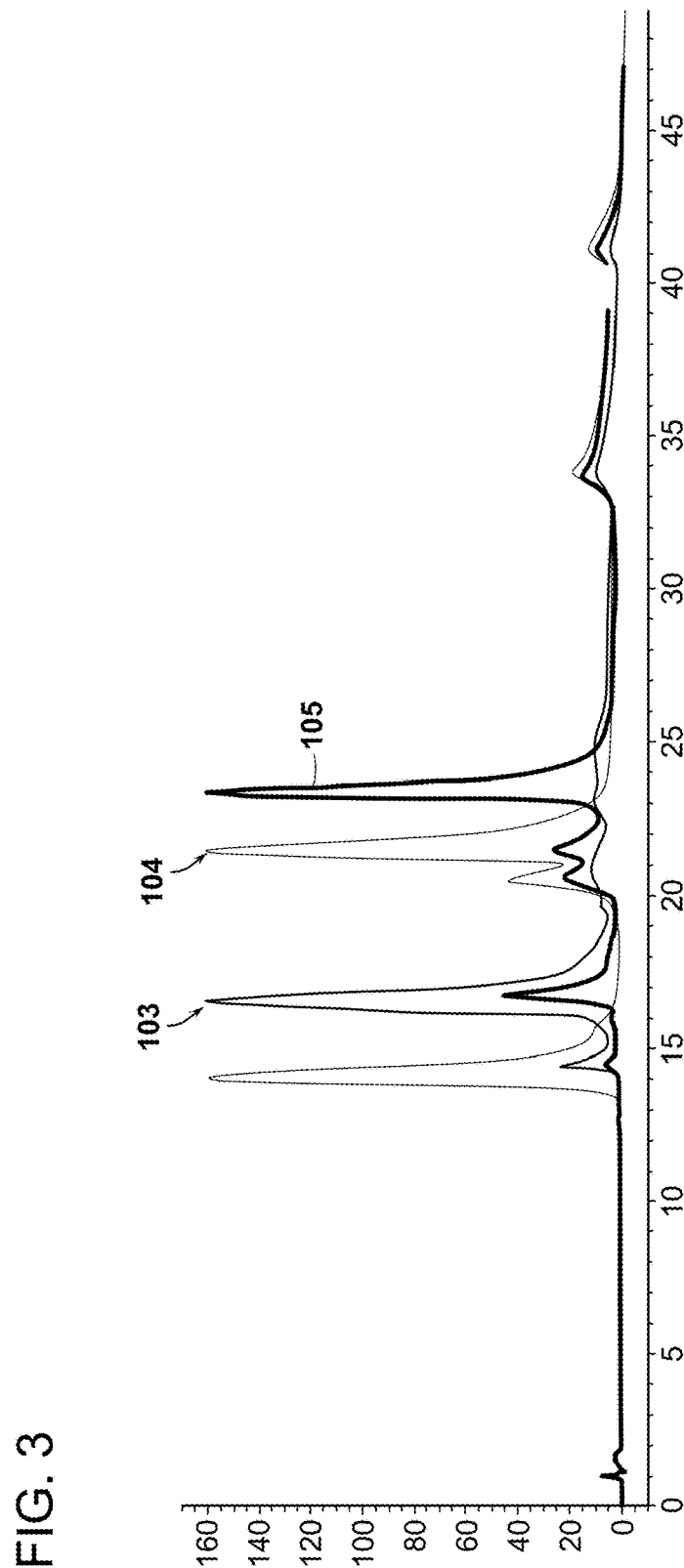
FIG. 3 illustrates a Hydrophobic Interaction Chromatography (HIC) analysis of bispecific antibody compound 105.

Agilent 1200 HPLC using a Tskgel Buytl-NPR 4.6mm× 10 cm 2.5 um was used to analyze the FAB$^1$-DBCO, FAB$^2$-azide and bispecific antibody compound product of Formula I. Buffer A: 50 mM NaH$_2$PO$_4$, 1.5M (NH$_4$)$_2$ SO$_4$ pH 7.0 and Buffer B: 50 mM NaH$_2$PO$_4$ pH 7.0+25%IPA. See FIG. 3. MS found molecular weight of 95954.00, theoretical 95955.00 for 105.

Bispecific antibody compounds of Formula I were purified via Size-exclusion chromatography (SEC) using an Agilent 1200 HPLC using a TSK gel SuperSW3000 column (4.6 mm ID×30 cm, 4 μm). Buffer was 0.2 M potassium phosphate, 0.25 M KCl, pH 6.2.

αPSMA/αCD3 Bispecific Antibody Compounds

Figure 10:
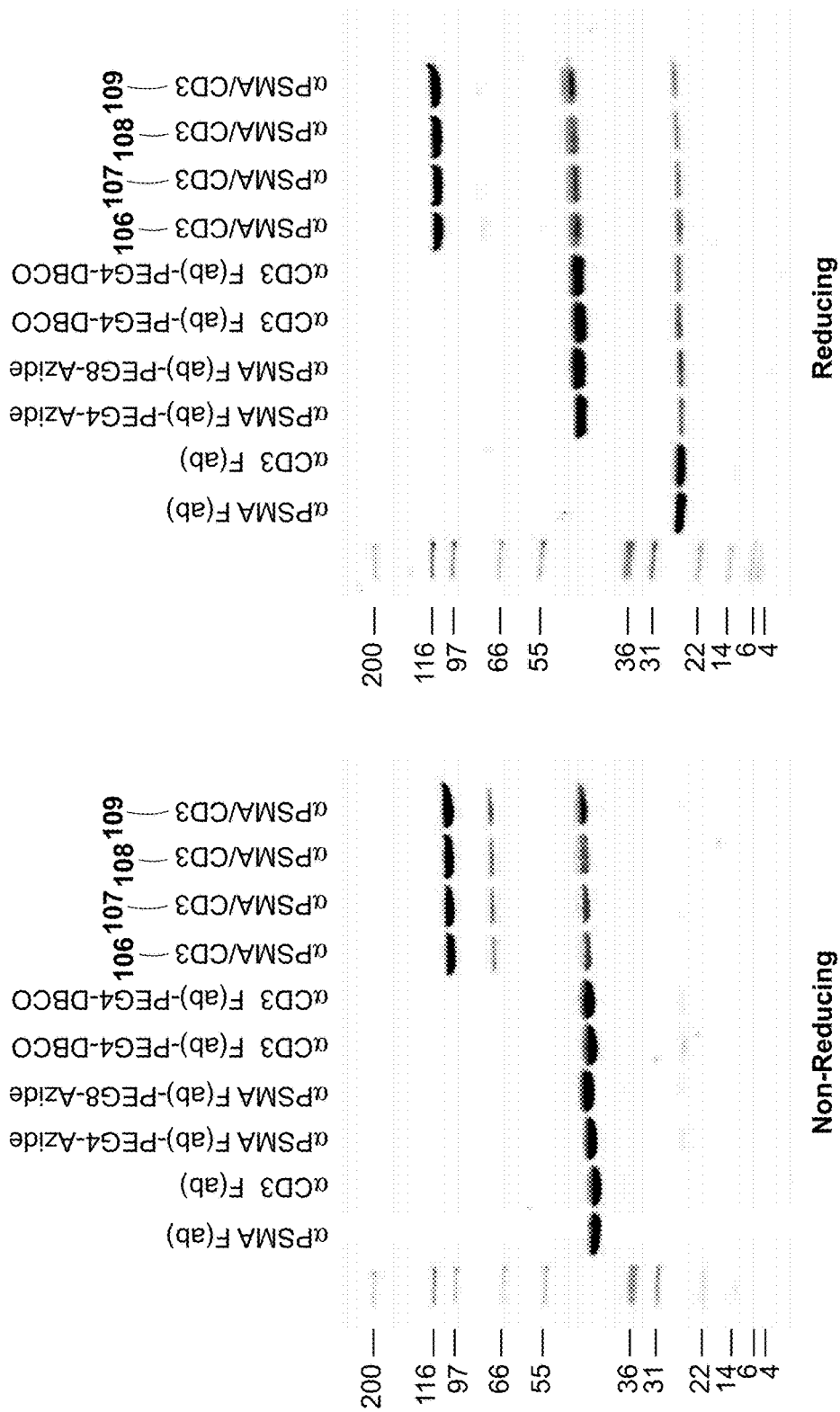
FIG. 10 shows the SDS-PAGE analysis of αPSMA/αCD3 bispecific antibody compounds 106, 107, 108, and 109.
Figure 11:
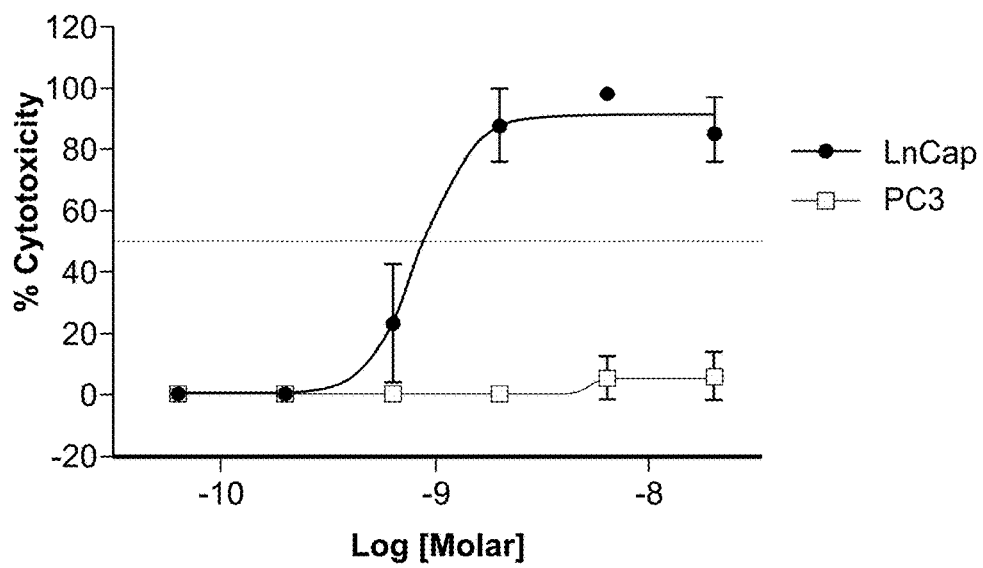
FIG. 11 shows % killing vs concentration of bispecific antibody compound 108 in LnCaP and PC3 Cells.
Figure 12:
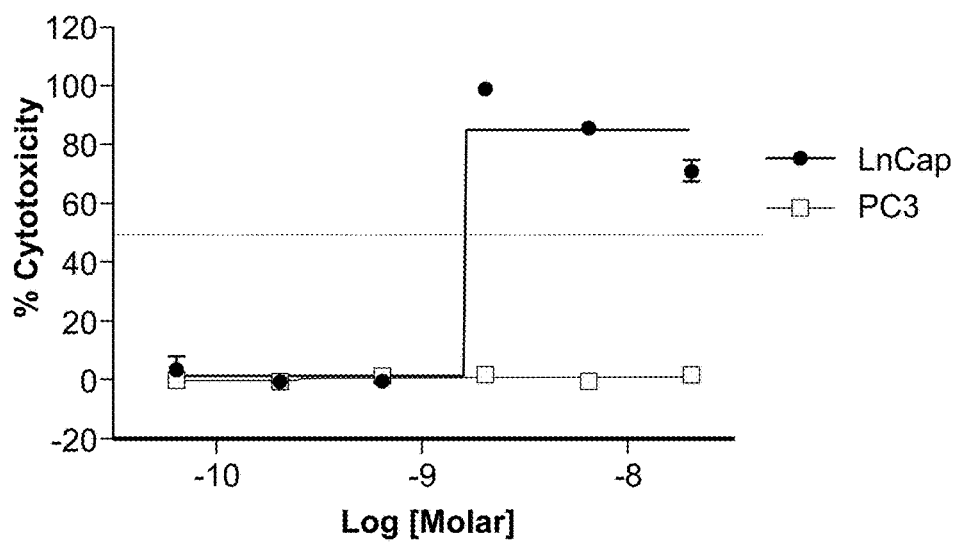
FIG. 12 shows % killing vs concentration of bispecific antibody compound 109 in LnCaP and PC3 Cells.

General Procedure for αPSMA-PEG4/αCD3-PEG4 (106), αPSMA-PEG4/αCD3-PEG8 (107), αPSMA-PEG8/αCD3-PEG4 (108) and αPSMA-PEG8/αCD3-PEG8 (109)

αPSMA-PEG4/αCD3-PEG4 (106), αPSMA-PEG4/αCD3-PEG8 (107), αPSMA-PEG8/αCD3-PEG4 (108) and αPSMA-PEG8/αCD3-PEG8 (109) were synthesized according to the methods described above, and using the appropriate starting materials. See also FIG. 7 for a general representation of the approach. For example, the azide linker was prepared in situ by reacting DBM-PEG4-DBCO and DBM-PEG8-DBCO linker with 10-15 equivalents azido-PEG2-azide for 1 h at room temperature (RT). F(ab) proteins (5 mg/mL) were typically reduced using 5 or 10 equivalents of DTT for 1 h at RT followed by conjugation with 10 or 15 equivalents DBM linker, respectively, and 7.5% DMSO co-solvent overnight at RT. Excess linker was removed by centrifugal filtration. Heavy chain-light chain disulfide bridging was determined to be ~85% efficient by SDS-PAGE and HIC HPLC analysis. Cyclization was initiated by mixing the αPSMA F(ab) intermediate and the αCD3 F(ab) intermediate at 5 mg/mL for 24-48 h at either room temperature or 37° C. Purity of the antibody and intermediates prior to cyclization were assessed by SDS-PAGE analysis and HIC HPLC. See FIG. 6, FIG. 8, and FIG. 9. The yield of the final products were ~65-95% yield depending on incubation temperature and time. Purity of bispecific products 106, 107, 108, and 109 were assessed by SDS-PAGE and shown in FIG. 10.

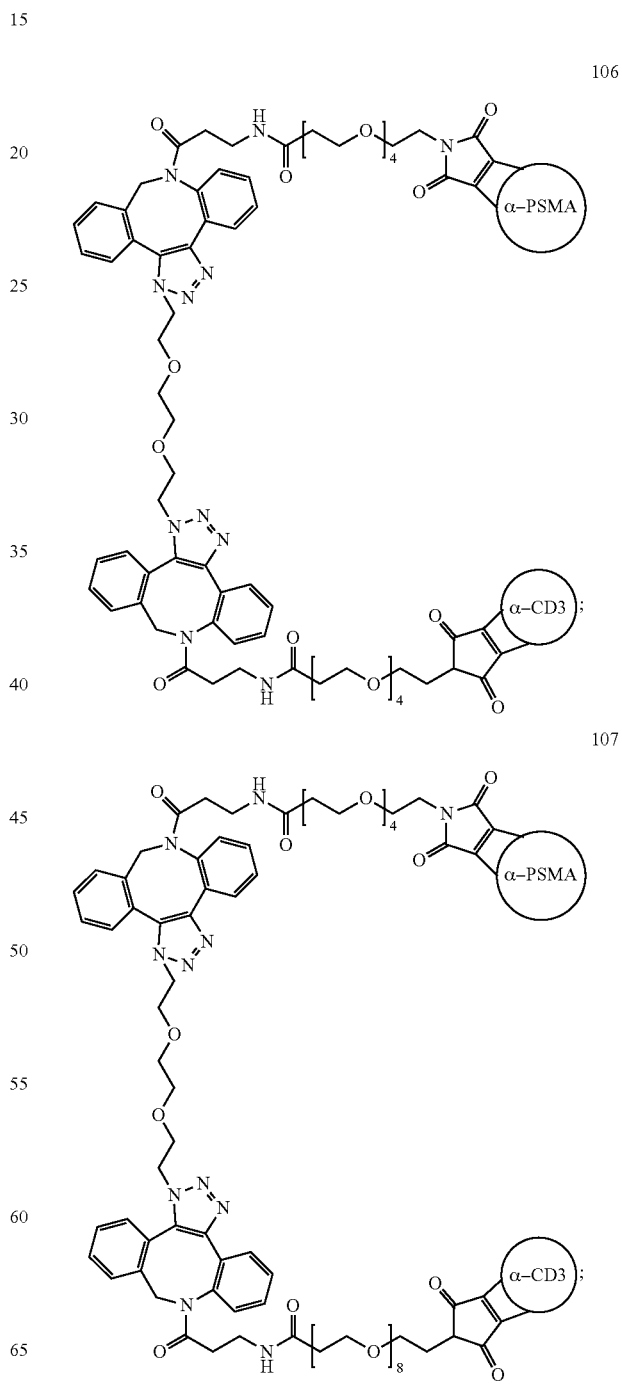

106

107

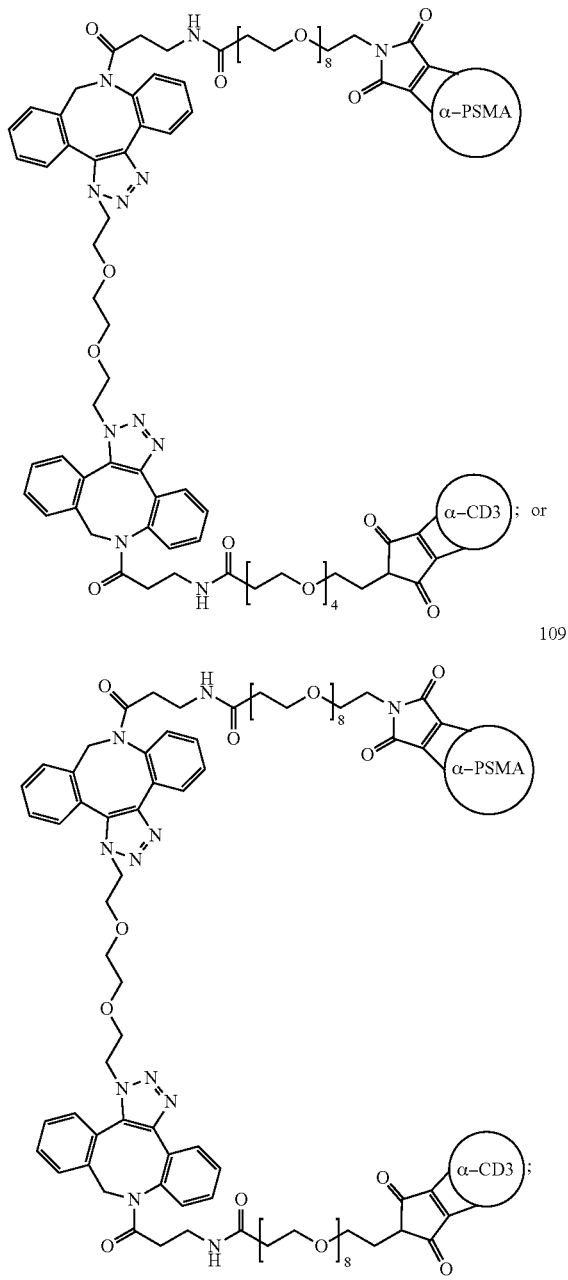

In Vitro Affinity Measurements using Octet Red

Figure 4:
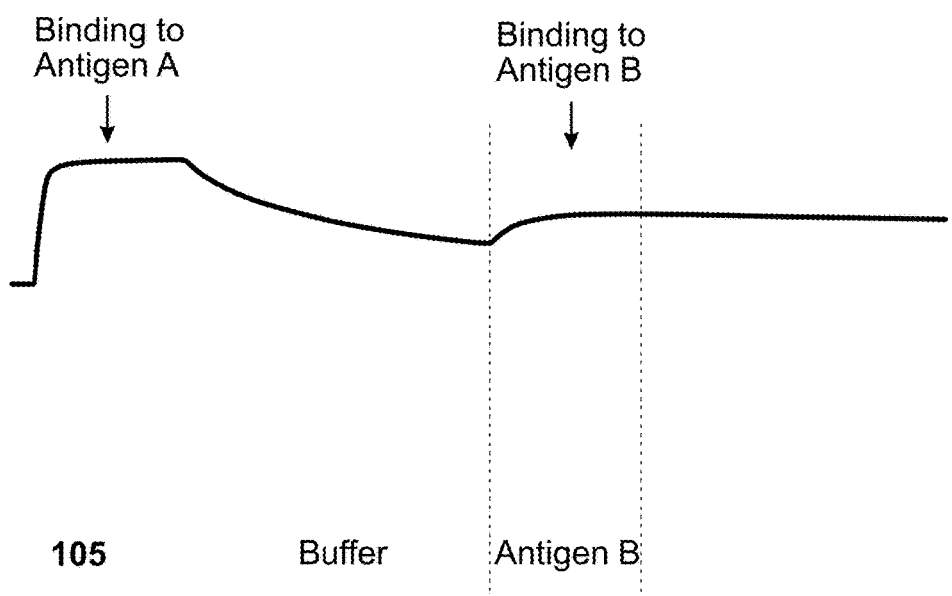
FIG. 4 illustrates simultaneous binding of bispecific antibody compound 105 to two antigens on Octet Red.

Sensors AR2G were used to measure antigen interactions with 105 on the Octet Red (ForteBio, Inc.) In short, the measurement scheme was as follows: 300 seconds baseline; 300 seconds loading of 10 µg/ml Antigen A, 120 seconds baseline; 300 seconds 105 ; 300 seconds dissociation; 300 seconds Antigen B and 300 seconds dissociation (FIG. 4). Sensor hydration and baseline- and dissociation measurements were performed in PBS. As described in FIG. 4, each Fab fragment was able to maintain antigen binding.

Luminescence Cytotoxicity Assay with Bispecific Antibody Compounds 108 and 109

Firefly luciferase transduced prostate cancer target cell lines were used for cytotoxicity assays, LNCaP (ATCC® CRL-1740™), PSMA+ (cultured in RPMI-1640+10% non-heat-inactivated FBS+0.5 µg/mL Puromycin) and PC-3 (ATCC® CRL-1435™), PSMA− (cultured in RPMI-1640+ 10% heat-inactivated FBS+1.0 µg/mL Puromycin). Cells were harvested with TrypLE (ThermoFisher Scientific) then resuspended in fresh RPMI-1640+10% heat-inactivated FBS and plated at 4,000 cells/well in 100 µL. After overnight incubation at 37° C. in a humidified 5% $CO_2$ incubator, serial dilutions of FAB and bispecific antibody compounds of Formula I in RPMI-1640 +10% heat-inactivated medium (50 µL) were added to the assay plates at the indicated concentrations. Freshly thawed peripheral blood mononuclear cells (PBMCs) were washed with media and added to the assay plates at 40,000 cells in 50 µL to obtain an effector:target ratio of 10:1. After 4 days incubation, 90 µL was removed from assay plates and 90 µL ONE Glo Luciferase Assay Reagent (Promega #E6120) was mixed with the samples and incubated at room temperature for 10 min. Samples were transferred to white 96-well flat bottom plates for luminescence measurements using a PerkinElmer EnSpire multimode plate reader. Data was analyzed using GraphPad Prism software. Cell killing was observed with compounds 108 and 109 at PSMA+ LNCaP cells with a potency of ~1 nM. Parental F(ab) proteins did not show cytotoxic activity. No bispecific antibody compound of Formula I-mediated cell killing was observed for PSMA-PC-3 cells. The data indicate that PSMA-directed cytotoxicity with bispecific antibody compound of Formula I was achieved using PBMCs at effector:target 10:1.

The invention claimed is:

1. A bispecific antibody compound having the Formula III or IIIa:

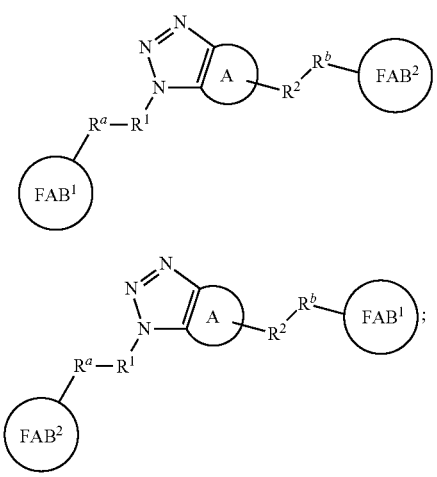

wherein:
FAB¹ represents a first Fab fragment;
FAB² represents a second Fab fragment;
R¹ and R² are each independently a substituted alkyl; ring A is a substituted carbocyclyl or substituted heterocyclyl;
$R^a$ and $R^b$ are each

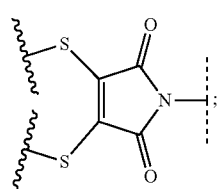

"⁓" indicates the points of attachment to FAB¹ or FAB²; and

"-----" indicates the point of attachment to R¹ or R².

2. The bispecific antibody compound of claim 1, wherein Ring A is a substituted bicyclic or polycyclic carbocyclyl or a substituted polycyclic heterocyclyl.

3. The bispecific antibody compound of claim 1, wherein: ring A is

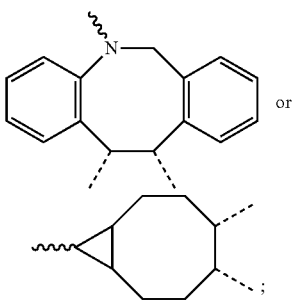

the dashed bonds indicate the points of attachment to the triazolyl; and
the wavy bond indicates the attachment to R².

4. The bispecific antibody compound of claim 1, wherein R¹ and R² are each independently an optionally substituted $(C_2-C_{30})$alkyl optionally interrupted with one or more heteroatoms selected from N, O, and S.

5. The bispecific antibody compound of claim 1, wherein R¹ and R² are each independently a substituted $(C_2-C_{30})$ alkyl optionally interrupted with one or more heteroatoms selected from N and O.

6. The bispecific antibody compound of claim 1, wherein R¹ and R² are each independently a $(C_2-C_{30})$alkyl interrupted with at least one O and at least one N, and substituted with at least one oxo.

7. The bispecific antibody compound of claim 1, wherein R¹ and R² are each independently selected from

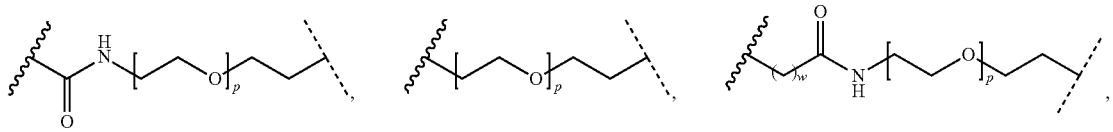

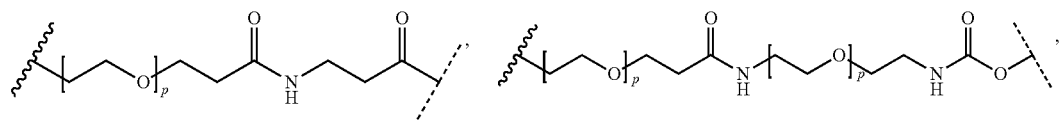
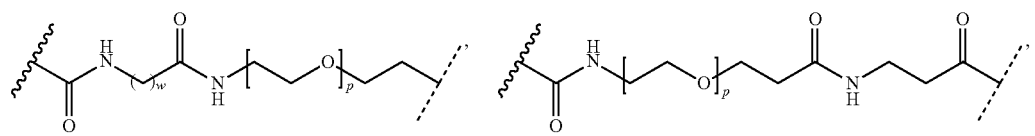
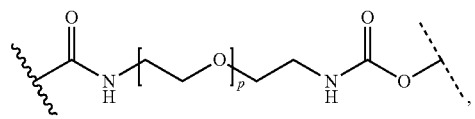
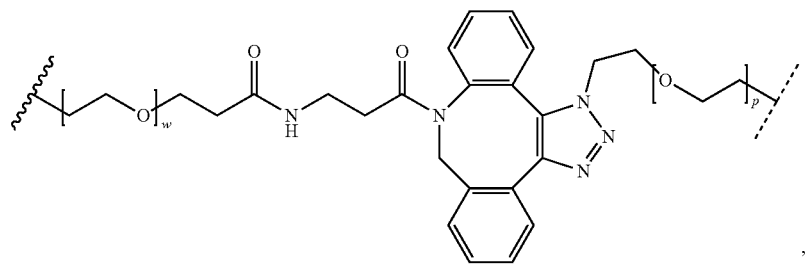
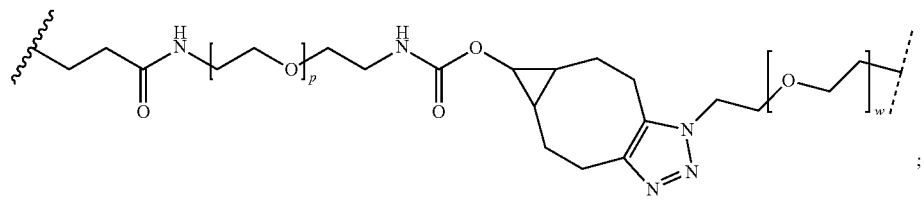
the wavy lines indicate the points of attachment to $R^a$ or $R^b$;
the dashed lines indicated the points of attachment to the triazolyl or ring A; and
p and w independently are integers from 1 to 8.
8. The bispecific antibody compound of claim 1, wherein $R^1$ is selected from
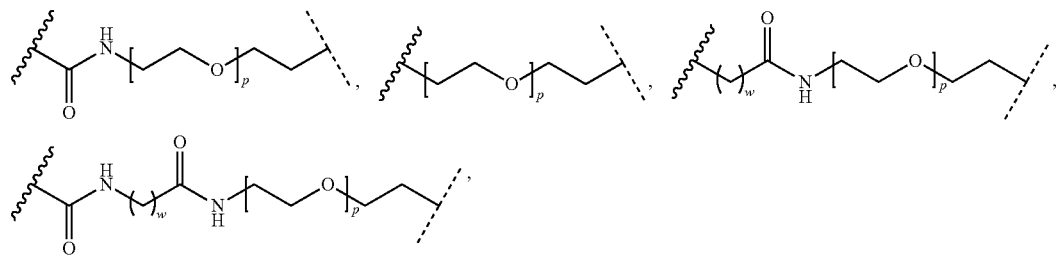

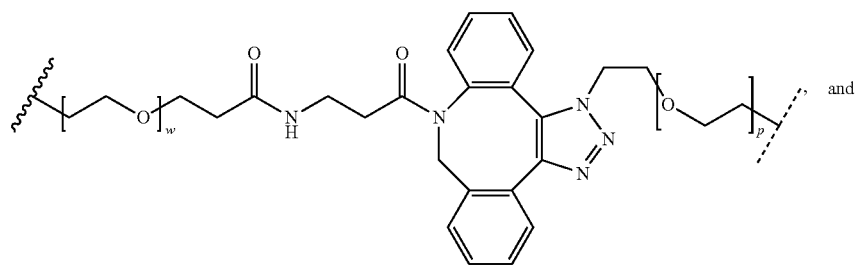

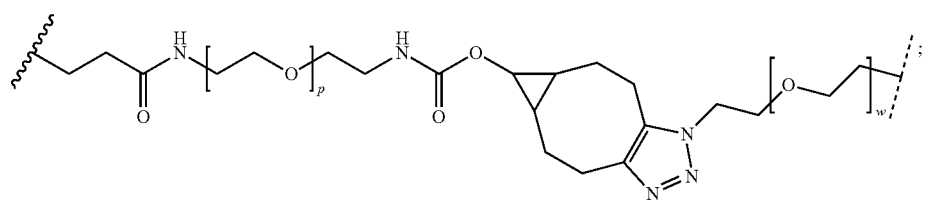

the wavy lines indicate the points of attachment to $R^a$; and the dashed lines indicated the points of attachment to the triazolyl; and p and w independently are integers from 1 to 8.

9. The bispecific antibody compound of claim 1, wherein $R^2$ is selected from

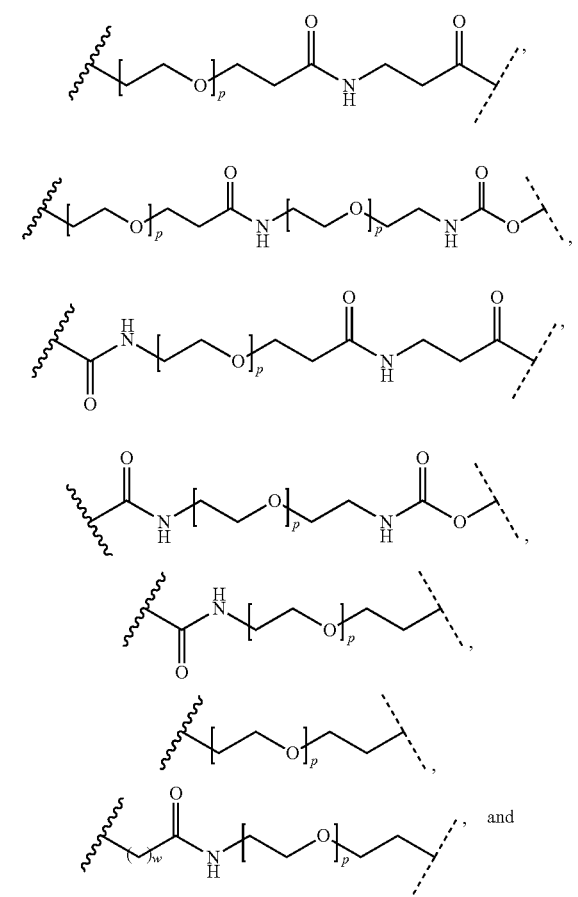

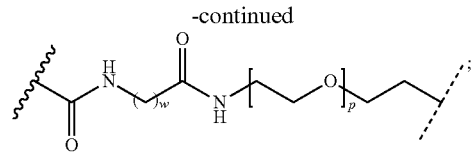

the wavy lines indicate the points of attachment to $R^a$; and the dashed lines indicated the points of attachment to the triazolyl or ring A; and p and w independently are integers from 1 to 8.

10. The bispecific antibody compound of claim 1, wherein $R^a$ and $R^b$ are bound to $FAB^1$ and $FAB^2$ through native cysteines of $FAB^1$ and $FAB^2$.

11. The bispecific antibody compound of claim 1, wherein the bispecific antibody of Formula III or Formula IIIa is of the formula:

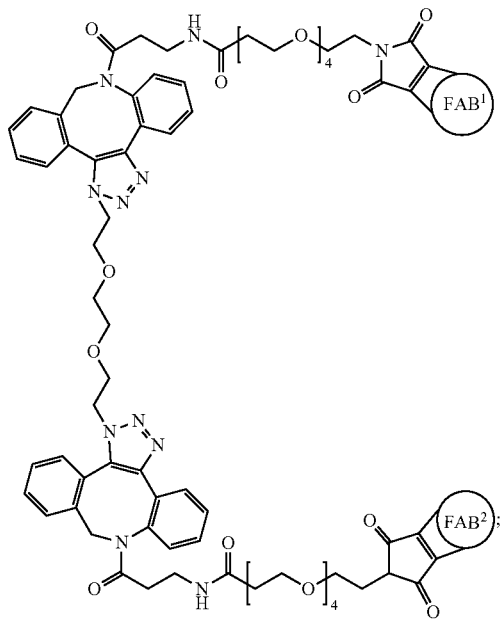

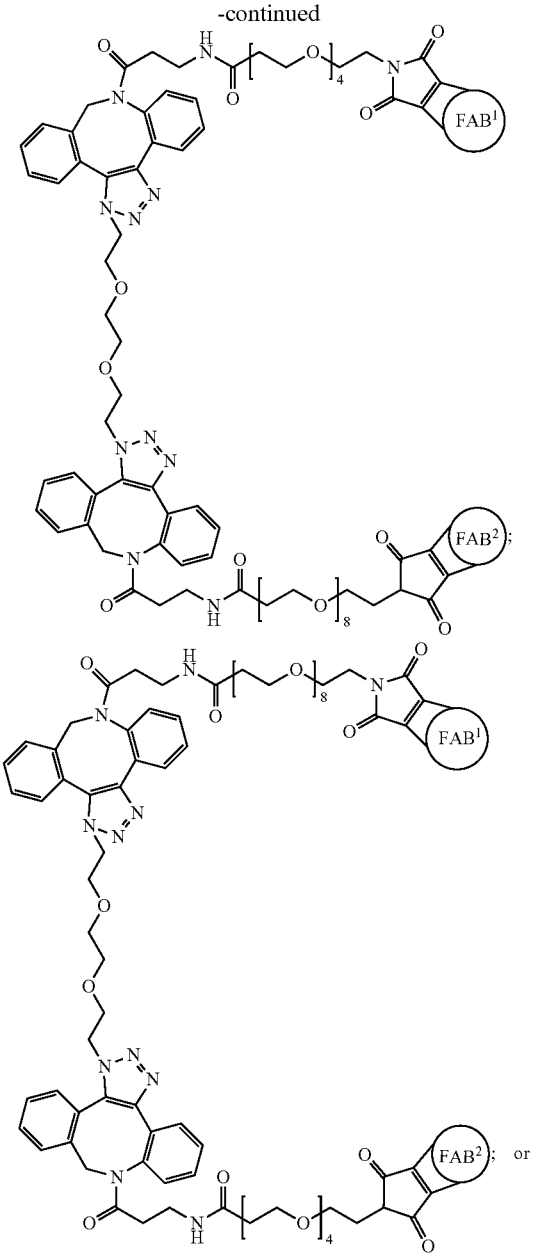

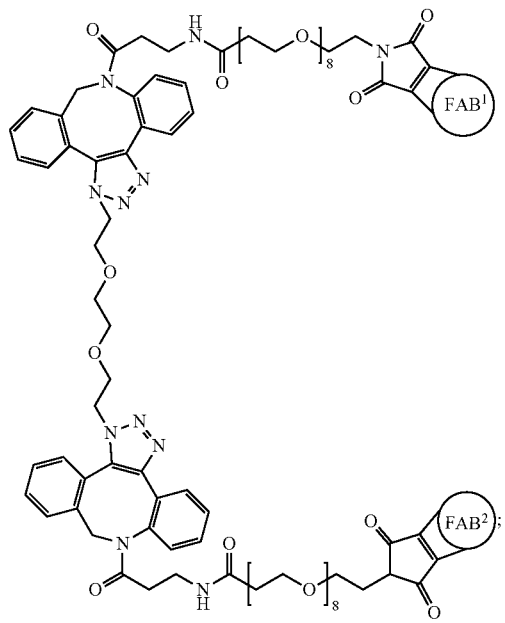

or a pharmaceutically acceptable salt thereof, wherein FAB¹ and FAB² are connected to the pyrrolidine-dione through native cysteine residues.

12. The bispecific antibody compound of claim 1, wherein FAB¹ and FAB² do not comprise a hinge region.

13. The bispecific antibody compound claim 1, wherein FAB¹ and FAB² are each independently selected from a Fab fragment comprising a CD3 binding region and a Fab fragment comprising a PSMA binding region.

14. A pharmaceutical composition comprising the bispecific antibody compound of claim 1; and a pharmaceutically acceptable carrier.

* * * * *

UNITED STATES PATENT AND TRADEMARK OFFICE
CERTIFICATE OF CORRECTION

PATENT NO. : 10,301,395 B2  
APPLICATION NO. : 15/353979  
DATED : May 28, 2019  
INVENTOR(S) : Fu et al.

Page 1 of 1

It is certified that error appears in the above-identified patent and that said Letters Patent is hereby corrected as shown below:

On the Title Page

Item [57], "used a modulators" should read --used as modulators--.

In the Claims

Column 53, Claim 7, Line 46, insert --wherein-- before "the" (first instance).

Column 53, Claim 7, Line 46, "indicated" should read --indicate--.

Column 55, Claim 8, Line 26, "indicated" should read --indicate--.

Column 56, Claim 9, Line 32, "indicated" should read --indicate--.

Column 58, Claim 13, Line 39, insert --of-- after "compound".

Signed and Sealed this  
Seventeenth Day of December, 2019

Andrei Iancu  
*Director of the United States Patent and Trademark Office*

SEQUENCE LISTING

<160> NUMBER OF SEQ ID NOS: 10

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Gln Met Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Tyr Ser Trp Val Arg Gln Ala Pro Gly Gln Gly Leu Glu Trp Met
            35                  40                  45

Gly Gly Ile Ile Pro Ser Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ile Val Ala Thr Ile Thr Pro Leu Asp Tyr Trp Gly
            100                 105                 110

Gln Gly Thr Leu Val Thr Val Ser Ser
            115                 120

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Leu Val Trp Asp Ser Ser Ser Asp His
                85                  90                  95

Arg Ile Phe Gly Gly Gly Thr Lys Leu Thr Val Leu
            100                 105

<210> SEQ ID NO 3
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Gln Val Gln Leu Val Gln Ser Gly Ala Glu Val Lys Lys Pro
1               5                   10                  15

Gly Ser Ser Val Lys Val Ser Cys Lys Ala Tyr Gly Gly Thr Phe Gly
            20                  25                  30

Ser Tyr Gly Val Ser Trp Val Arg Arg Ala Pro Gly Gln Gly Leu Glu
            35                  40                  45

Trp Met Gly Arg Leu Ile Pro Ile Phe Gly Thr Arg Asp Tyr Ala Gln
        50                  55                  60

```
Lys Phe Gln Gly Arg Val Thr Leu Thr Ala Asp Glu Ser Thr Asn Thr
 65                  70                  75                  80

Ala Tyr Met Glu Leu Ser Ser Leu Arg Ser Glu Asp Thr Ala Val Tyr
                 85                  90                  95

Tyr Cys Ala Arg Asp Gly Asp Tyr Tyr Gly Ser Gly Ser Tyr Tyr Gly
            100                 105                 110

Met Asp Val Trp Gly Gln Gly Thr Leu Val Thr Val Ser Ser
            115                 120                 125

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Thr Thr Leu Thr Gln Ser Pro Ala Thr Leu Ser Val Ser Pro Gly
  1               5                  10                  15

Glu Arg Ala Thr Val Ser Cys Arg Ala Ser Gln Ser Leu Gly Ser Asn
                 20                  25                  30

Leu Gly Trp Phe Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Phe Cys Gln Gln Tyr Asn Asp Trp Pro Ile
                 85                  90                  95

Thr Phe Gly Gln Gly Thr Arg Leu Glu Ile Lys
            100                 105

<210> SEQ ID NO 5
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Ile Ser Tyr
                 20                  25                  30

Thr Met His Trp Val Arg Gln Ala Pro Gly Gln Gly Leu Glu Trp Met
             35                  40                  45

Gly Tyr Ile Asn Pro Arg Ser Gly Tyr Thr His Tyr Asn Gln Lys Leu
 50                  55                  60

Lys Asp Lys Ala Thr Leu Thr Ala Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Ala Ser Thr Lys Gly Pro Ser Val
            115                 120                 125
```

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr
225

<210> SEQ ID NO 6
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 7
<211> LENGTH: 230
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr
225                 230

<210> SEQ ID NO 8
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95
```

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser
        115                 120

<210> SEQ ID NO 10
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

```
Ala Leu Ile Asn Pro Tyr Lys Gly Val Ser Thr Tyr Asn Gln Lys Phe
    50              55                  60

Lys Asp Arg Phe Thr Ile Ser Val Asp Lys Ser Lys Asn Thr Ala Tyr
 65             70                  75                  80

Leu Gln Met Asn Ser Leu Arg Ala Glu Asp Thr Ala Val Tyr Tyr Cys
                85                  90                  95

Ala Arg Ser Gly Tyr Gly Asp Ser Asp Trp Tyr Phe Asp Val Trp
            100             105             110

Gly Gln Gly Thr Leu Val Thr Val Ser Ser
        115             120
```